(12) United States Patent
Tapinos et al.

(10) Patent No.: US 12,060,557 B2
(45) Date of Patent: Aug. 13, 2024

(54) TARGETING ENHANCER RNAS FOR THE TREATMENT OF PRIMARY BRAIN TUMORS

(71) Applicants: Brown University, Providence, RI (US); Rhode Island Hospital, Providence, RI (US)

(72) Inventors: Nikolaos Tapinos, Barrington, RI (US); Blessing Akobundu, Providence, RI (US)

(73) Assignees: Brown University, Providence, RI (US); Rhode Island Hospital, Providence, RI (US)

( * ) Notice: Subject to any disclaimer, the term of this patent is extended or adjusted under 35 U.S.C. 154(b) by 0 days.

(21) Appl. No.: 18/043,511

(22) PCT Filed: Sep. 1, 2021

(86) PCT No.: PCT/US2021/048671
§ 371 (c)(1),
(2) Date: Feb. 28, 2023

(87) PCT Pub. No.: WO2022/051365
PCT Pub. Date: Mar. 10, 2022

(65) Prior Publication Data
US 2023/0323349 A1  Oct. 12, 2023

Related U.S. Application Data

(63) Continuation of application No. PCT/CT2021/048671, filed on Sep. 1, 2021.

(60) Provisional application No. 63/073,177, filed on Sep. 1, 2020.

(51) Int. Cl.
| C12N 15/11 | (2006.01) |
| A61P 35/00 | (2006.01) |
| C12N 15/113 | (2010.01) |
| C12N 15/86 | (2006.01) |

(52) U.S. Cl.
CPC ............ *C12N 15/113* (2013.01); *A61P 35/00* (2018.01); *C12N 15/86* (2013.01); *C12N 2310/113* (2013.01); *C12N 2310/122* (2013.01); *C12N 2310/3231* (2013.01); *C12N 2310/341* (2013.01); *C12N 2740/15043* (2013.01)

(58) Field of Classification Search
None
See application file for complete search history.

(56) References Cited

U.S. PATENT DOCUMENTS

| 9,518,261 B2 | 12/2016 | Freier et al. |
| 10,160,977 B2 | 12/2018 | Hnisz et al. |
| 2015/0337376 A1 | 11/2015 | Saint-Andre et al. |
| 2019/0040395 A1 | 2/2019 | Freier |
| 2019/0062752 A1 | 2/2019 | Young et al. |
| 2020/0208128 A1 | 7/2020 | Bumcrot et al. |

FOREIGN PATENT DOCUMENTS

| EP | 2708601 A1 | 3/2014 |
| WO | 2013075233 A1 | 5/2013 |
| WO | 2014138983 A1 | 9/2014 |
| WO | 2018204764 A1 | 11/2018 |
| WO | 2019183552 A2 | 9/2019 |
| WO | 2019195854 A1 | 10/2019 |
| WO | 2019195855 A1 | 10/2019 |
| WO | 2020002691 A1 | 1/2020 |

OTHER PUBLICATIONS

"International Search Report and Written Opinion received for PCT Patent Application No. PCT/US2021/048671, mailed on Feb. 18, 2022", 16 pages.

"Invitation to Pay Additional Fees received for PCT Patent Application No. PCT/US2021/048671, mailed on Dec. 14, 2021", 3 pages.

Chen, et al., "Identification of Potential Crucial Genes and Molecular Mechanisms in Glioblastoma Multiforme by Bioinformatics Analysis", Molecular Medicine Reports, vol. 22, No. 2, Aug. 2020, pp. 859-869.

Genbank, "Penicillium Expansum Hypothetical Protein (PEX2_090530), Partial mRNA", Accession No. XM_016746323.1, Aug. 28, 2017, 2 pages.

Karambizi, et al., "RNA Epigenetics in Glioblastoma: Role of miRNA, lncRNA, eRNA and RNA Methylation", JSM Brain Science. vol. 3, No. 1, 2018, pp. 1-8.

Li, et al., "Targeting Long Noncoding RNA in Glioma: A Pathway Perspective", Molecular Therapy—Nucleic Acids, vol. 13,, Dec. 7, 2018, pp. 431-441.

Liang, et al., "Epstein-Barr Virus Super-Enhancer eRNAs are Essential for MYC Oncogene Expression and Lymphoblast Proliferation", Proceedings of the National Academy of Sciences of the United States of America, vol. 113, No. 49, Dec. 6, 2016, pp. 14121-14126.

Ling, et al., "MicroRNAs and Other Non-Coding RNAs as Targets for Anticancer Drug Development", Nature Reviews Drug Discovery, vol. 12,, Nov. 2013, pp. 847-865.

(Continued)

*Primary Examiner* — Ekaterina Poliakova-Georgantas
(74) *Attorney, Agent, or Firm* — Adler Pollock & Sheehan P.C.

(57) ABSTRACT

The invention provides enhancer RNAs (eRNAs) that are expressed specifically in glioma stem cells and whose expression correlates with decreased survival of patients with glioblastomas. The eRNAs are selected, for example, from eTMEM88b, eRTP5, or eNINJ1. The invention also provides an RNA therapy that targets glioma stem cell eRNAs using synthetic oligonucleotides that knock out the eRNA expression. The invention further provides viral vectors that deliver shRNA that inhibit the expression of the eRNA.

4 Claims, 8 Drawing Sheets

Specification includes a Sequence Listing.

(56) References Cited

OTHER PUBLICATIONS

Pandey, et al., "Functionally Enigmatic Genes: A Case Study of the Brain Ignorome", PLOS One, vol. 9, No. 2, Feb. 2014, 2 pages.
Rynkeviciene, et al., "Non-Coding RNAs in Glioma", Cancers, 2019, vol. 11, No. 17, 2019, 35 pages.
Wang, "An ASO Modification that Enhances Nuclease Resistance, Lowers Toxicity, and Increases Binding Affinity", Integrated DNA Technology, Jun. 27, 2018, 6 pages.

TARGETING ENHANCER RNAS FOR THE TREATMENT OF PRIMARY BRAIN TUMORS

FIELD OF THE INVENTION

This invention generally relates to vector systems having a special element relevant for transcription being an enhancer not forming part of the promoter region.

REFERENCE TO RELATED APPLICATIONS

This application is a national phase filing under 35 U.S.C. § 371 of International Patent Application no. PCT/US2021/048671, filed on Sep. 1, 2021, which claims priority to U.S. provisional patent application Ser. No. 63/073,177, filed on Sep. 1, 2020 the entire contents of which are hereby incorporated by reference herein.

BACKGROUND OF THE INVENTION

Glioblastoma is the most prevalent primary brain tumor and one of the most aggressive and lethal cancers. Treatment for glioblastomas includes surgical resection of the tumor mass followed by radiation and temozolomide administration. Stupp et al., N Engl. J. Med., 352, 987-996 (2005). But even with this multi-therapeutic approach, tumor recurrence is inevitable. Stupp & Weber, Onkologie, 28, 315-317 (2005). The aggressiveness attributed to glioblastomas is mainly driven by a population of glioma stem cells (GSCs) within the tumor mass that exhibits high migratory potential, resistance to chemotherapy and radiation, and possess the ability to form secondary tumors. Singh et al., Cancer Res., 63, 5821-5828 (2003); Singh et al., Nature, 432, 396-401 (2004); Lee et al., Cancer Cell 9, 391-403 (2006); and Soni et al., Asian Pac. J. Cancer Prev., 18, 2215-2219 (2017).

Glioma stem cells exhibit remarkable plasticity, can transition between immature and differentiated stages, and can reversibly express various phenotypic markers, depending on the tumor microenvironment. Ben-Porath et al., Nature Genetics, 40, 499-507 (2008); and Jin et al., Nature Medicine, 23, 1352-1361 (2017).

There remains a need in the art for compositions and methods for better treating gliomas.

SUMMARY OF THE INVENTION

The invention targets molecular mechanisms that control glioma stem cell plasticity and affect glioblastoma growth.

In the first embodiment, the invention provides enhancer RNAs (eRNAs) expressed specifically in glioma stem cells and whose expression correlates with decreased survival of patients with glioblastomas. In the second embodiment, the eRNAs are selected from the group consisting of eTMEM88b, eRTP5, and eNINJ1, as shown in the SEQUENCE LISTING below.

In the third embodiment, the invention provides an RNA therapy. The therapy targets glioma stem cell eRNAs using synthetic oligonucleotides that knockout the expression of the eRNA. In the fourth embodiment, the synthetic oligonucleotides are resistant to degradation.

In the fifth embodiment, the invention provides a viral vector that delivers an shRNA that targets and inhibits the expression of the eRNA. In the sixth embodiment, the viral vector is a lentivirus.

The invention has several advantages. In the first aspect, regarding the target specificity, the targeted eRNAs are expressed specifically in glioma stem cells. In the second aspect, regarding drug specificity, the synthesized oligonucleotides or viral vectors are specific for the intended target eRNA. The synthesized oligonucleotides or viral vectors do not have a substantial effect on other genes. In the third aspect, regarding resistance to degradation, the oligonucleotide RNA-therapeutic is chemically modified to be resistant to degradation. The oligonucleotide RNA-therapeutic works for in vivo applications. In the fourth aspect, regarding the specific effect on glioma stem cells, the inhibition of the target eRNA results in reduced expression of transcription factors that define the cancer stem cell phenotype like Nanog, Oct6, and Sox2. This result shows that eRNA targeting can affect cancer stemness, tumor propagation, and aggression.

The genome-wide data analysis has shown there are fifteen glioma stem cell-specific eRNAs compared to differentiated cells. Further analysis has shown these eRNAs are differentially expressed across at least seven glioma stem cells, and high expression of three eRNAs correlates significantly with poor patient survival. Preliminary results on inhibition of one of the three clinically-relevant eRNAs show that inhibition may be important for regulating glioma stem cell essential genes.

BRIEF DESCRIPTION OF THE DRAWINGS

FIG. 2(A) is a bar chart showing that glioma stem cells express the stem cell-specific transcripts CD133, Sox2, and Olig2, which they lose entirely (CD133, Olig2) or downregulate (Sox2) after differentiation for seven days by removal of EGF, bFGF and Heparin and addition of 10% serum. The differentiated glioma cells gain expression of GFAP, which was not expressed in glioma stem cells. The bar chart presents representative RNA-seq data from one glioma stem cell line. The analysis was performed for all glioma stem cells and differentiated glioma cells. FIG. 2(B) is a chart showing the results of a limiting dilution assay to determine the self-renewal ability of glioma stem cells. The assays were repeated six times, and significance was calculated with a Chi-square test (p<0.008).

DETAILED DESCRIPTION OF THE INVENTION

Industrial Applicability

Figure 1:
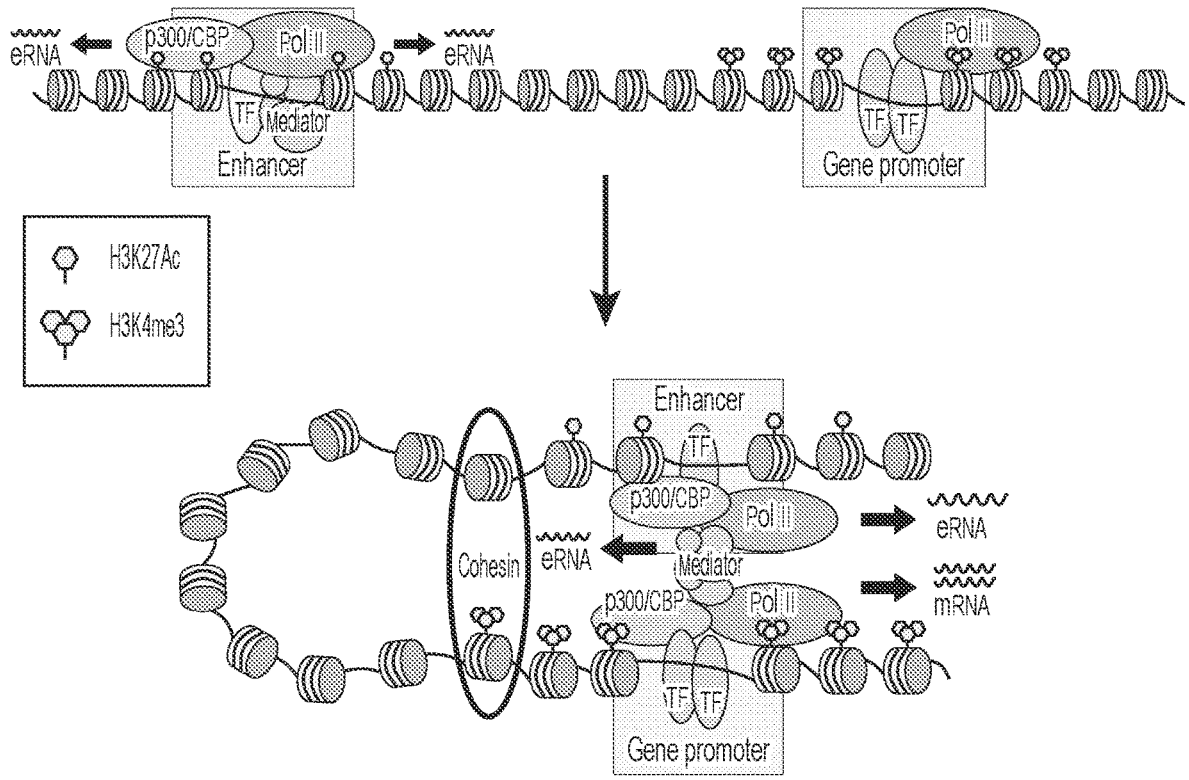
FIG. 1 is a schematic drawing of eRNA in regulating transcription. The enhancer region (blue box) is marked by H3K27Ac and loaded with transcription factors (TF) and RNA Pol II helping to produce eRNAs in a bidirectional manner. The promoter region (purple box) is marked by H3K4me3 and transcription factors. Looping of enhancer to promoter mediated by Cohesin and Mediator complex brings eRNAs to close proximity with the promoter to induce transcription of the target gene.

Glioblastoma Multiforme remains one of the most challenging diseases to treat. There is currently no glioma stem cell-specific therapy for glioblastoma. Standard treatments include surgery, followed by combinatorial radiotherapy and chemotherapy. Although conventional GBM therapies have been beneficial to some patients, the average tumor recurrence time is seven months.

Information on epigenetic abnormalities such as DNA methylation, histone modifications, and non-coding RNAs are being evaluated as drivers of cancer, including Glioblastoma Multiforme. See Feng et al., Methods Mol. Biol., 1165, 115-43 (2014).

Using cutting-edge genome-wide technology such as ChIP-seq to identify glioma stem cell-specific eRNAs has shown that eRNAs are essential for glioma stem cell maintenance. The invention provides a way for eRNAs to be a stem cell-specific therapy for Glioblastoma Multiforme. The specific target of eRNAs using Locked Nucleic Acid GapmeRs provides a glioma stem cell-specific, RNA-based therapeutic option for glioblastoma patients.

The successful manipulation of the glioma stem cell-specific eRNAs can benefit the procuring a promising glioma stem cells-specific RNA-based therapy for Glioblastoma Multiforme patients. This specification shows how to determine the functional role of glioma stem cell-specific eRNAs in Glioblastoma Multiforme. See EXAMPLE 2 below. This specification also explains how to determine the contribution of eRNAs to the maintenance of chromatin states in glioma stem cells. See EXAMPLE 3 below. This specification further shows how to evaluate the efficacy of eRNAs as glioma stem cell-specific therapeutic targets. See EXAMPLE 4 below.

Definitions

For convenience, the meaning of some terms and phrases used in the specification, examples, and appended claims, are listed below. Unless stated otherwise or implicit from context, these terms and phrases have the meanings below. These definitions are to aid in describing particular embodiments and are not intended to limit the claimed invention. Unless otherwise defined, all technical and scientific terms have the same meaning as commonly understood by a person having ordinary skill in the molecular neurobiological art or biotechnological art or both arts. For any apparent discrepancy between the meaning of a term in the art and a definition provided in this specification, the meaning provided in this specification shall prevail.

"ATAC-seq" or Assay for Transposase-Accessible Chromatin using sequencing is a molecular biology technique to assess genome-wide chromatin accessibility. See Buenrostro et al., Transposition of native chromatin for fast and sensitive epigenomic profiling of open chromatin, DNA-binding proteins, and nucleosome position. Nature Methods, 10(12), 1213-8 (December 2013).

"Brain tumor" has the neurobiological art-recognized meaning of a growth of abnormal cells in or derived from the tissues of the brain. Brain tumors can be benign (not cancer) or malignant (cancer). See the National Cancer Institute Dictionary of Cancer Terms.

"ChIP-seq" or ChIP-sequencing is a method used to analyze protein interactions with DNA. ChIP-seq combines chromatin immunoprecipitation (ChIP) with massively parallel DNA sequencing to identify the binding sites of DNA-associated proteins.

Figure 2:
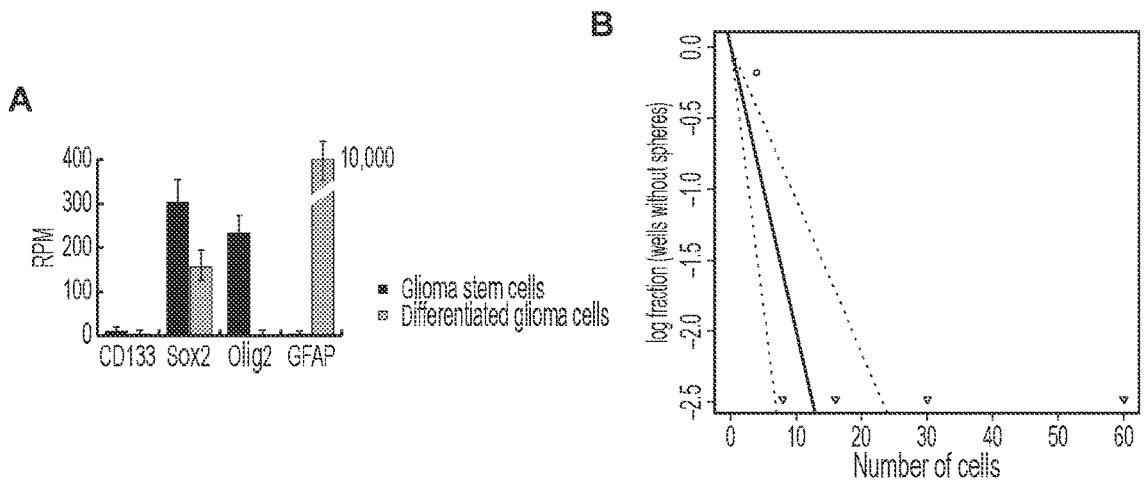
FIG. 2 shows a characterization of glioma stem cells and differentiated glioma cells.

"Differentiated glioma cells" (DGCs) have the neurobiological art-recognized meaning of glioma cells differentiated from stem cells. The molecular and genetic classifications of Glioblastoma Multiforme and treatment approaches to Glioblastoma Multiforme have relied predominantly on differentiated glioma cells. In laboratory practice, differentiated glioma cells gain expression of GFAP, which marker was not expressed in glioma stem cells. See, Bramanti et al., Biomarkers of glial cell proliferation and differentiation in culture. Front. Biosci. (Schol. Ed.), 2, 558-70 (2010). See also FIG. 2(A) description, above.

"Enhancer RNA" (eRNA) has the molecular biological art-recognized meaning of a member of a class of relatively short non-coding RNA molecules (50-2000 nucleotides) transcribed from the DNA sequence of enhancer regions. See FIG. 1. The stem-specific eRNAs are named according to the genes in their closest vicinity and denoted with an "e" prefix throughout this specification.

"GapmeR" has the biotechnological art-recognized meaning of short DNA antisense oligonucleotide structures with RNA-like segments on both sides of the sequence. These linear pieces of genetic information are designed to hybridize to a target piece of RNA and silence the gene through the induction of RNase H cleavage. Binding of the gapmer to the target has a higher affinity due to the modified RNA flanking regions, as well as resistance to degradation by nucleases. See Stein et al., Nucleic Acids Res., 38(1), e3 (2010); Crooke et al., Antisense technology: an overview and prospectus. Nature Reviews Drug Discovery, 1-27 (Mar. 24, 2021).

"Glioblastoma Multiforme" brain tumor (GBM) has the neurobiological art-recognized meaning of a fast-growing glioma that develops from star-shaped glial cells (astrocytes and oligodendrocytes) that support the health of the nerve cells within the brain. GBM is often called a grade IV astrocytoma. See National Cancer Institute (NCI) Dictionary of Cancer Terms.

"Glioma stem cell" (GSC)— also known as glioblastoma stem cells for this specification—has the neurobiological art-recognized meaning of self-renewing, tumorigenic cancer stem cells present in glioblastoma and that contribute to tumor initiation and therapeutic resistance. Glioma stem cells exhibit "phenotypic plasticity" which is important because the different cellular states of Glioblastoma Multiforme (stem and differentiated states) are believed by persons having ordinary skill in the molecular neurobiological art to contribute to tumor mechanism and aggression. In laboratory practice, glioma stem cells known markers of stemness, including oligodendrocyte transcription factor (Olig2), Sox2, and prominin-1 (CD133). See Yan et al., Endothelial cells promote the stem-like phenotype of glioma cells through activating the Hedgehog pathway. J. Pathol., 234(1), 11-22 (2014). See also FIG. 2(A) description, above.

"H3K27Ac" has the molecular biological art-recognized meaning of an epigenetic modification to the DNA packaging protein Histone H3. It is a mark that indicates the acetylation at the 27th lysine residue of the histone H3 protein. H3K27ac is associated with the higher activation of transcription and therefore defined as an active enhancer mark. H3K27ac is found at both proximal and distal regions of the transcription start site (TSS).

"H3K4me3" has the molecular biological art-recognized meaning of an epigenetic modification to the DNA packaging protein Histone H3. It is a mark that indicates the tri-methylation at the 4th lysine residue of the histone H3 protein and often involved in regulating gene expression. The name denotes the addition of three methyl groups (trimethylation) to the lysine 4 on the histone H3 protein.

"Lentivirus viral vector" has the molecular biological art-recognized meaning of a replication-defective viral vector that comprises a sequence of RNA or DNA nucleotides derived from a lentivirus.

"NINJ1" or Ninjurin 1 is a protein-coding gene. Diseases associated with NINJ1 include Hereditary Sensory Neuropathy and Non-Functioning Pancreatic Endocrine Tumor. An important paralog of this gene is NINJ2. Several identification numbers are GCID: GC09M093121, HGNC: 7824, Entrez Gene: 4814, Ensembl: ENSG00000131669, OMIM: 602062, and UniProtKB: Q92982.

"Non-coding RNAs" have the molecular biological art-recognized meaning of RNA species that are not templates for protein and include: ribosomal RNA (rRNA), microRNA (miRNA), long non-coding RNA (lncRNA) and other forms produced at different regions in the genome. See, Costa, Non-coding RNAs: Meet thy masters. Bioessays, 32(7), 599-608 (2010), and Guttman et al., Chromatin signature reveals over a thousand highly conserved large non-coding RNAs in mammals. Nature, 458(7235), 223-7 (2009).

"Primary brain tumor" has the molecular neurobiological art-recognized meaning of a tumor that develops in a brain. Primary brain tumors are classified by type and the World Health Organization (WHO) grade. Doctors often diagnose primary brain tumors by performing a computerized tomography (CT) scan or magnetic resonance imaging (MRI). A full medical exam may also performed and a detailed medical history taken to help doctors plan the best course of management. When human brain tumors are near "eloquent" parts of the brain with important function (i.e., speech and motor areas), a more specialized MRI can be performed by neuroradiologists to better understand the relationship between the tumor and the function in the brain.

"RTP5" or Receptor Transporter Protein 5 (Putative) is a protein-coding gene. Diseases associated with RTP5 include Venous Hemangioma and Amyotrophic Lateral Sclerosis 7. Among its related pathways are Signaling by GPCR and Olfactory transduction. An important paralog of this gene is RTP3. Several identification numbers are GCID: GC02P241869, HGNC: 26585, Entrez Gene: 285093, Ensembl: ENSG00000188011, and UniProtKB: Q14D33

"shRNA" or short hairpin ribonucleic acids have the molecular biological art-meaning of an artificial RNA molecule with a tight hairpin turn that can silence target gene expression via RNA interference (RNAi). Paddison et al., Genes & Development, 16(8), 948-58 (April 2002); Brummelkamp et al., Science, 296(5567), 550-3 (April 2002). The expression of shRNA in cells is typically accomplished by the delivery of plasmids or through viral or bacterial vectors. shRNA is an advantageous mediator of RNAi because it has a relatively low rate of degradation and turnover.

"TMEM88B" or Transmembrane Protein 88B is a protein-coding gene. Diseases associated with TMEM88B include Alexithymia. Several identification numbers are GCID: GC01P001426, HGNC: 37099, Entrez Gene: 643965, Ensembl: ENSG00000205116, and UniProtKB: A6NKF7.

"Viral vector" has the molecular biological art-recognized meaning of a nucleic acid vector construct that includes at least one viral origin element and can be packaged into a viral vector particle. The viral vector can contain the nucleic acid encoding a polypeptide or nucleic acid in place of non-essential viral genes. The vector or particle can transfer any nucleic acids into cells either in vitro or in vivo. Many viral vectors are known in the molecular biological art.

Guidance from Materials and Methods

A person having ordinary skill in the molecular neurobiological art can use the following patents, patent applications, and scientific references as guidance to predictable results when making and using the invention:

To ensure rigor and reproducibility, the inventors repeat assays using at least three biological replicates.

eRNA inhibition assay. The effects of eRNA inhibition are compared to glioma stem cells treated with scrambled GapmeRs. Representation of all subtypes is useful for identifying patients who benefit from GapmeR RNA-based therapy.

Cell death assay. Apoptotic cell death is quantified in real-time using the Incucyte live-cell analysis system to measure the cleavage of Caspase-3/7. The assay uses inert, non-fluorescent substrates that freely cross the cell membrane, where they can be cleaved by activated caspase-3/7 to release either a green or red DNA-binding fluorescent label. The appearance of fluorescently-labeled nuclei identifies apoptotic cells.

Proliferation assay. The proliferation rate of cells in culture is quantified in real-time using the Incucyte Cell-by-Cell Analysis Software Module. This label-free, direct cell count allows for identifying individual cells by counting the number of phase objects over time. Cells are classified into subpopulations based on properties such as size and shape.

Self-renewal assay. The ability of glioma stem cells to self-renew is analyzed using the in-vitro extreme limiting dilution analysis (ELDA).

Luciferase reporter assay. Several luciferase assays are commercially available.

Method of Manufacture

In a seventh commercial embodiment, a person having ordinary skill in the biotechnological art can use Qiagen's online algorithm to design the antisense oligonucleotide GapmeR. Qiagen (Hilden, Germany) can then synthesize the custom GapmeR for in vivo applications. Qiagen can synthesize proprietary chemical modifications, so that the antisense oligonucleotides remain stable and resistant to degradation.

Method of Treatment

The method of treatment is based upon the methods of Southwell et al., Trends in Molecular Medicine, 18(11) (November 2012) and several other papers. Oligonucleotide as therapy can be efficiently and safely delivered with intrathecal injections, intra parenchymal, or cerebrospinal fluid (CSG) delivery.

In an eighth particular embodiment, the administration of RNA therapeutics to the brain is intrathecal. In our case, the inventors favor the intrathecal injection in humans or primates. For the rodent models, the inventors use injection in the lateral ventricle, so the GapmeR is delivered through the cerebrospinal fluid.

Pharmaceutical Compositions

One or more of the pharmaceutical and liposomal compositions (e.g., lipid nanoparticles) comprise one or more of the compounds disclosed herein and one or more additional lipids. For example, lipid nanoparticles that comprise or are otherwise enriched with one or more of the compounds disclosed herein may further comprise one or more of DOTAP (1,2-dioleyl-3-trimethylammonium propane), DODAP (1,2-dioleyl-3-dimediylammonium propane), DOTMA (1,2-di-0-octadecenyl-3-Irimethylammonium propane), DLinDMA, DLin-KC2-DMA, Cl2-200 and ICE. In a ninth embodiment, the pharmaceutical composition comprises a lipid nanoparticle that comprises HGT4001, DOPE and DMG-PEG2000. In tenth embodiment, the pharmaceutical composition comprises a lipid nanoparticle that comprises HGT4003, DOPE, cholesterol and DMG-PEG2000.

One or more of the pharmaceutical compositions described herein may comprise one or more PEG-modified lipids. For example, lipid nanoparticles that comprise or are otherwise enriched with one or more of the compounds disclosed herein may further comprise one or more of PEG-modified lipids that comprise a poly(ethylene)glycol chain of up to 5 kDa in length covalently attached to a lipid comprising one or more $C_6$-$C_{20}$alkyls.

Similarly, the pharmaceutical compositions (e.g., lipid nanoparticles) may comprise or may otherwise be enriched with one or more of the compounds disclosed herein and may further comprise one or more of helper lipids selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), DOPE (1,2-dioleoyl-swglycero-3-phosphoethanolamine), DSPE (1,2-distearoyl-s/i-glycero-3-phosphoethanolamine), DLPE (1,2-dilauroylglycero-3-phosphoethanolamine), DPPS (1,2-dipalmitoyl-sn-glycero-3-phospho-L-serine), ceramides, sphingomyelins and cholesterol.

The following EXAMPLES are provided to illustrate the invention and should not be considered to limit its scope.

Example 1

An Oligonucleotide GapmeR that Inhibits the Target eRNA.

To discover eRNAs expressed specifically in glioma stem cells, the inventors used two patient-derived glioma stem cells that represent the mesenchymal (GSC1) and proneural (GSC2) subtypes of the TOGA-based Verhaak classification scheme. To obtain differentiated glioma cells, the inventors subjected the glioma stem cells to a seven-day differentiation process. They performed transcript expression analysis for glioma stem cells and differentiated cell markers. See FIG. 2(A). All glioma stem cell samples demonstrated self-renewal potential during limiting dilution assays. See FIG. 2(B). After transplantation into immunocompromised mice, the glioma stem cells showed tumor-forming ability.

To identify which eRNAs glioma stem cells specifically express, the inventors performed ChIP-seq using ChIP-validated antibodies against H3K27Ac for active enhancers, and RNAPII for active transcription (Active Motif). Peak calling representing genome-wide antibody binding was achieved for both H3K27Ac and RNAPII in all samples. The subsequent analysis included the removal of overlap with mRNA production; the association of RNAPII and H3K27Ac peak overlaps as putative eRNA production regions; the identification of individual sample-specific eRNAs; the selection of peaks within 10,000 nucleotides (10K) upstream and downstream of the identified putative eRNA sites as these regions best associate with the genes of interest; the isolation of common peaks between the two glioma stem cell and differentiated glioma cell samples; and discovery of unique peaks within the stem and differentiated samples. The unique peaks were defined as RNAPII and H3K27Ac peaks. The inventors observed that the peaks align and overlap exactly within the same enhancer peak boundary. The computational filtration analysis allowed the narrowing of the results down to fifteen eRNAs unique to the two glioma stem cells and twenty-one eRNAs unique to the two differentiated glioma cells.

To validate the expression of the glioma stem cell-specific eRNAs, the inventors performed RT-qPCR using RNA isolated from seven additional patient-derived glioma stem cells (GSC) and two neural stem cell (NSC) lines (H9 & H14 derivatives). The individual eRNAs had varied expression patterns within and across the glioma stem cell samples.

The inventors then probed for the expression of the genes corresponding to all fifteen eRNAs. The inventors observed that the expressions were all amplified in glioma stem cells at varying levels.

Figure 5:
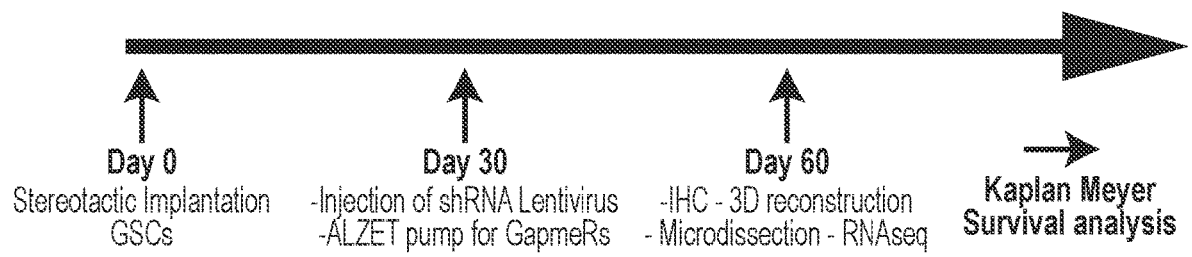
FIG. 5 is a schematic representation of developing eRNA therapeutics in vivo efficacy measurements.
Figure 6:
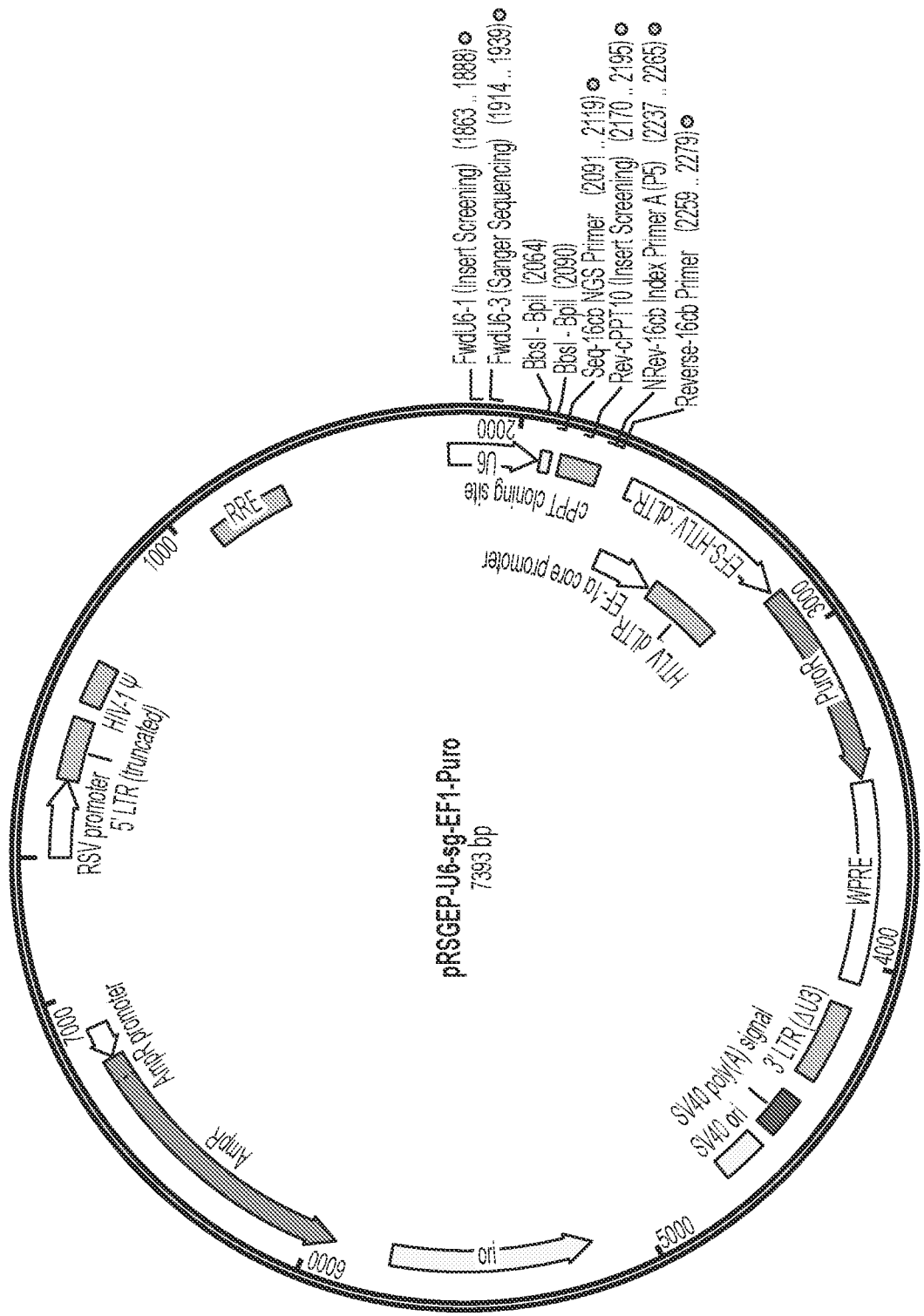
FIG. 6 is a schematic representation of the lentivirus vector pRSGEP-U6-sg-EF1-Puro.

Next, the inventors determined the expression of the eRNAs in seventy Glioblastoma Multiforme tissue samples available from the Department of Pathology at Rhode Island Hospital. The inventors probed for fourteen eRNAs instead of fifteen eRNAs because the RT-qPCR results showed that one of the eRNAs [eDAP3] was low or not expressed in various glioma stem cell samples. Using NanoString Technology and their nSolver™ Analysis Software, the inventors generated an eRNA expression heatmap for the seventy Glioblastoma Multiforme tissue samples with high (indicated by red) and low (blue) across all samples. See, e.g., FIG. 5. The inventors correlated the tissue expression of the eRNAs to the survival of patients using the standardized log-rank statistics and maximally selected rank statistics.

Figure 3:
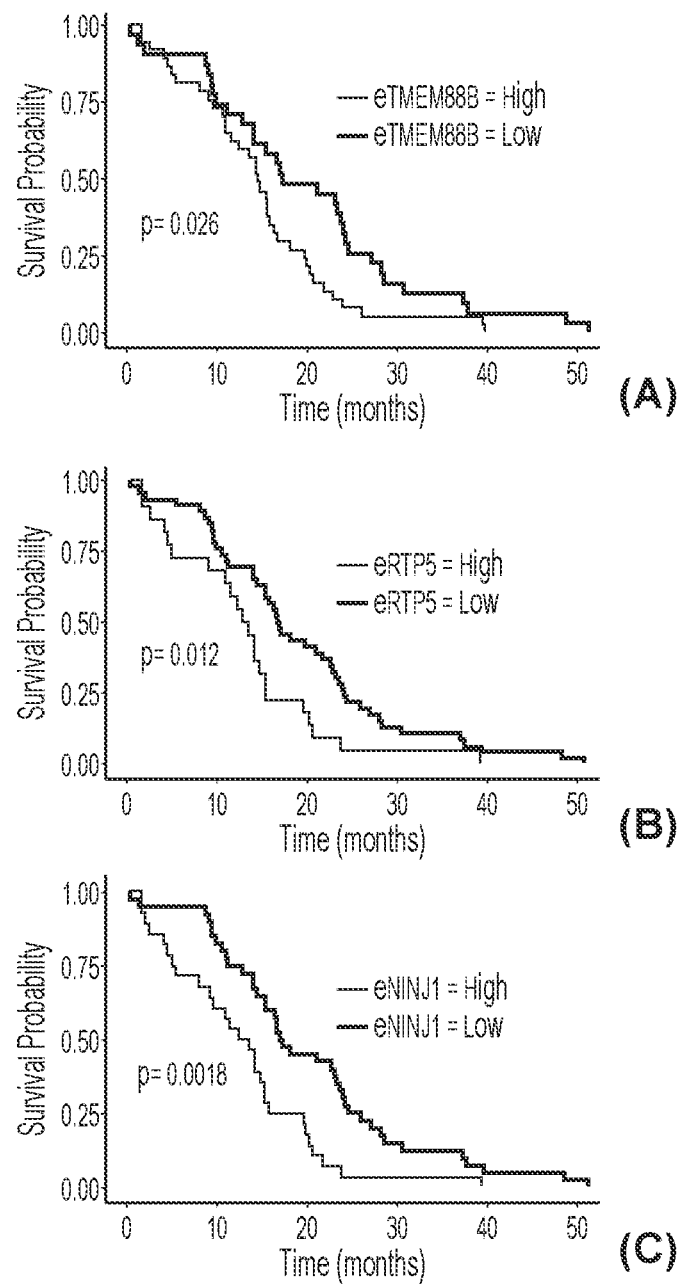
FIG. 3 shows comparing survival time in patients with high expression versus low expression of the three glioma stem cell-specific eRNAs. The three Kaplan-Meyer survival curves showing overall patient survival in correlation with eTMEM888 (A), eRTP5 (B), and eNINJ1 (C) eRNAs. The survival time was collected from clinical data of the seventy IDH-wild type glioblastoma patients (Rhode Island Hospital, Departments of Neurosurgery and Pathology). High expression of these eRNAs correlates significantly with lower survival of patients with glioblastoma (p<0.05).
Figure 4:
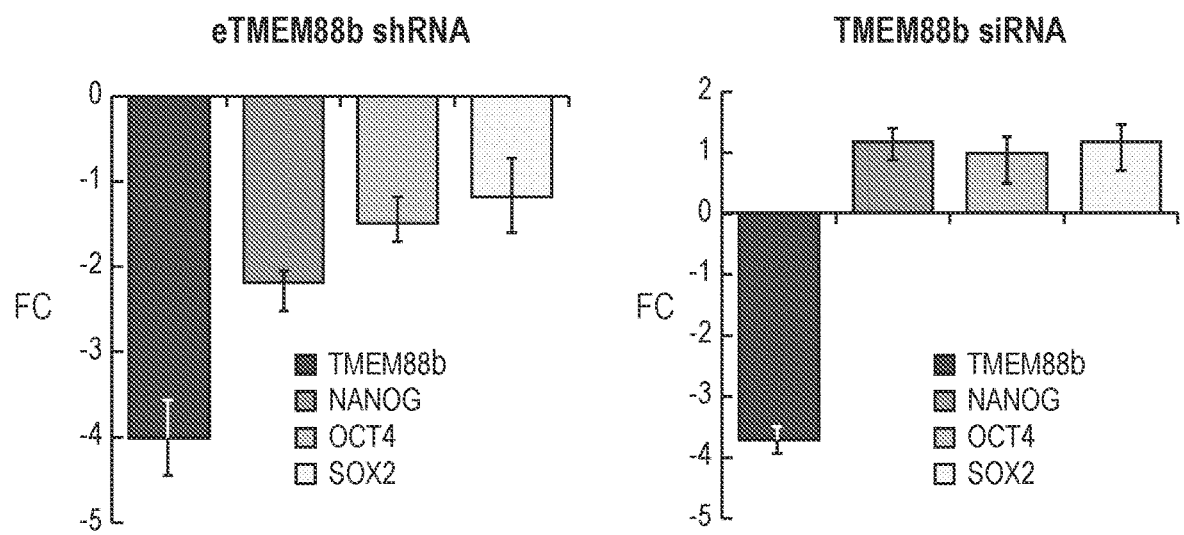
FIG. 4 is a pair of bar graphs showing the inhibition of eTMEM888 and TMEM88B gene. The chart on the left shows the inhibition of eTMEM888 with an Antisense Oligo GapmeR results in inhibition of TMEM88B, NANOG, OCT4, and SOX2 expression. The chart on the right shows the inhibition of TMEM88B mRNA using siRNAs results in inhibition of TMEM88B expression but does not affect NANOG, OCT4, and SOX2.

Patients with high expression of eTMEM88B (Transmembrane Protein 88B), eRTP5 (Receptor Transporter Protein 5), and eNINJ1 (Nerve Injury-Induced Protein), presented with worst survival at statistically significant levels compared to low expressors. See FIG. 3.

Example 2

Determining the Functional Relevance of Glioma Stem Cell-Specific eRNAs for Glioblastoma Multiforme The inventors use a pharmacological approach to analyze the effect of eRNA inhibition on apoptosis, proliferation, self-renewal, and differentiation of glioma stem cells. The inventors inhibit three clinically relevant eRNAs and then check the effect of inhibition.

Inhibition of eRNA and functional analysis to check for the effect of inhibition on glioma stem cells. In EXAMPLE 1, using one glioma stem cell sample and two concentrations of Locked Nuclei Acid GapmeRs, targeting eTMEM888 has shown promising knockdown of this eRNA in a concentration-dependent manner. The inventors repeat this inhibition for the other two eRNAs: eRTP5 and eNINJ1.

Figure 8:
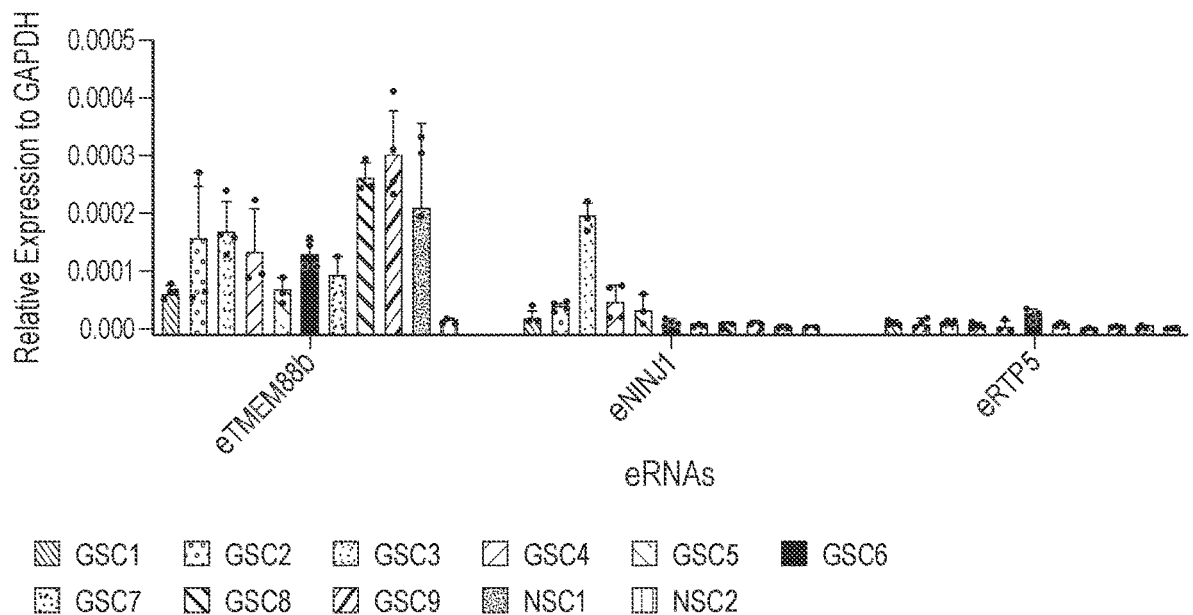
FIG. 8 is a bar graph showing the expression of eTMEM88b, eNINJ1, and eRTP5 in nine patient-derived glioma stem cells and two human neural stem cell samples.

The following assays can show whether inhibition of eRNAs affects glioma stem cell viability, proliferation, self-renewal, and differentiation:

Additional mechanism of eRNA effects on glioma stem cells. Regarding the functional role of eRNAs in glioma stem cells, the inventors determine how the reported functions are due to the eRNA per se or the cognate gene, TMEM88B. The inventors performed separate single tests where the expression levels of three essential stem-cell genes (NANOG, OCT4, SOX2) upon eTMEM888 inhibition using the GapmeR and inhibition of TMEM88B gene were examined, using a pool of siRNAs. These results showed that inhibition of eTMEM888 results in a significant knockdown of the cognate gene, TMEM88B, especially at the higher concentration of 5 µM. Furthermore, the inventors observed slight inhibition of NANOG, OCT4, and SOX2 despite GapmeR dose. The knockdown of the TMEM88B gene with siRNAs does not affect NANOG, OCT4, and SOX2 expression. See, FIG. 8.

Thus, eTMEM888 expression has a specific role in regulating not only its cognate gene but also in stemness gene expression in glioma stem cells.

The inventors also investigate other parameters of the eRNA effect on glioma stem cells, such as checking for changes in important promoter regions using a luciferase reporter assay.

Alternative strategies. Inhibition using the GapmeR involved a direct cellular uptake method called gymnosis. This method only showed ~50% knockdown. Therefore, the inventors can use an alternative method such as optimized lipid transfection to increase the GapmeR uptake and achieve a higher knockdown for all eRNA targets. Since each glioma stem cell sample has its own unique cultural needs, the inventors can troubleshoot their transfection protocol to determine the optimal conditions for each sample empirically.

Example 3

Determine the Contribution of eRNAs to Changes in Chromatin States of Glioma Stem Cells The manipulation of eRNAs can modulate the chromatin state of glioma stem cells. The inventors use a combination of Assay for Transposase-Accessible Chromatin with high-throughput sequencing (ATAC-seq), and Chromatin Immunoprecipitation coupled with high-throughput sequencing (ChIP-seq) genome-wide sequencing tools to test this manipulation. This work is to determine the function of eRNAs as epigenetic regulators of cellular plasticity and cancer stemness.

Research approach. Effects of eRNAs on chromatin accessibility. To determine genome-wide chromatin accessibility patterns, the inventors perform ATAC-seq in glioma stem cells following inhibition of eRNA and compare to ATAC-seq data from control glioma stem cells (treated with scrambled GapmeRs). Data analysis is performed to discover how inhibition of eRNA expression affects global chromatin accessibility over gene regulatory regions. The inventors determine chromatin accessibility over promoter and enhancer regions and functionally cluster the closest genes to the differentially accessible promoters and enhancers.

Effects of eRNAs on transcription regulation. The higher-order eukaryotic genome functional architecture structures and their associated sub-nuclear compartments are recognized by those of ordinary skill in the molecular neurobiological art as the key components contributing to many aspects of nuclear activities, including DNA transcription. Scientific publications have shown that eRNAs augment gene transcription through interaction with various general cofactors, such as CBP, Mediator, BRD4, and Cohesin. To discover the role of the glioma stem cell-specific eRNAs in this transcriptional mechanism, the inventors can perform ChIP-seq for Mediator, cohesin, and CBP and BRD4, respectively, following knockdown of eRNA expression with oligonucleotide GapmeRs as described above.

Alternative strategies. Persons having ordinary skill in the molecular neurobiological art have experience in performing and analyzing ATAC-seq and ChIP-seq. Persons having ordinary skill in the molecular neurobiological art also have experience with an alternative analysis strategy, such as the publicly-available ChromHMM package, to annotate distinct "chromatin states" in the genome of the glioma stem cell samples. The ChromHMM package uses a multivariate hidden Markov model and epigenomic marks given as inputs to identify these chromatin states based on markers absent or present at genomic regions and the spatial relationship of these marks.

Example 4

Evaluate the Efficacy of eRNAs as RNA-Therapeutics.

Glioblastoma Multiforme therapies face many challenges, especially hindrance of drug passage through the blood-brain barrier (BBB). The inventors chemically modified and stable Locked Nucleic Acid GapmeRs that are in-vivo ready to inhibit our target eRNAs. Next, the inventors evaluate the efficacy of inhibition on tumor growth and size using Magnetic Resonance Imaging (MRI) and changes in stem-cell essential gene transcripts using RNA-seq.

To determine the efficacy of eRNA inhibition as a potential therapeutic for glioma stem cells, the inventors perform in vivo studies using orthotopic xenograft models of human glioblastoma. eRNAs may be adequate therapeutic targets for glioma stem cells owing to the identification of a specific group of eRNAs in glioma stem cells and not in their differentiated progeny.

Research Approach. Tumor generation and treatment with eRNA GapmeRs. The inventors can implant our patient-derived glioma stem cells (200,000 cells/mouse) into Nu/J mice under stereotaxic guidance, as described by Zepecki et al., Oncogene (2018). The inventors then allow tumors to grow for a month and then insert a microscopic catheter into the lateral ventricle connected to an osmotic pump (Alzet) to continuously deliver in vivo stable GapmeRs against the targeted eRNAs. See FIG. 5. To compare the efficacy of the treatment, the inventors use twelve mice for the non-treated control group, twelve mice for the scrambled GapmeR negative control group, and twelve mice for the eRNA-targeting GapmeR treated group.

Assays designed (twelve mice per group for each assay). Quantify inhibition for each eRNA and check for expression of stem and differentiation markers. The inventors check for successful inhibition of the target eRNAs using RT-qPCR and examine the changes in stem and differentiated markers: CD44 and GFAP respectively to ensure that in-vivo analyses are due to the inhibition of the eRNAs.

Determine the effect of eRNA inhibition on tumor volume. The inventors can stain serial sections of the brain of mice with HuNu antibody (Abcam) to accurately detect human glioma cells and perform 3D reconstruction and quantification of tumor volume, as shown before by Zepecki et al., Oncogene (2018).

The inventors micro-dissect tumors following a one-month treatment with the eRNA targeting GapmeR and perform RNAseq to determine the effect of eRNA inhibition on the glioblastoma transcriptome. As described in EXAMPLE 2, in vitro inhibition of eRNA results in inhibition of stemness gene expression. The treated tumors should express a less aggressive transcriptomic signature than control tumors.

Relevance to therapies for Glioblastoma Multiforme. Nucleic acid modifications and drug carriers are under development for the delivery of therapeutic molecules to the central nervous system. Alternatively, delivery of therapeutic molecules to the central nervous system can be accomplished by surgical techniques including intraventricular delivery of therapeutics via pumps, convection-enhanced delivery to brain parenchyma for drugs, and direct stereotactic injections of virus or cells remain the technique of choice currently.

Direct targeting of important eRNAs in Glioblastoma Multiforme is attractive for several reasons. First, a low copy number of eRNAs expressed in cells versus mRNAs ensures that fewer inhibitory GapmeRs are necessary to achieve eRNA inhibition. Second, eRNAs impact chromatin accessibility and modify gene expression patterns. Third, eRNAs represent an important node in the alteration of gene expression patterns. Fourth, eRNA expression patterns are linked to the clinical survival of Glioblastoma Multiforme patients in TOGA and other large RNA seq databases.

Alternative strategies. The Alzet pump intraventricular delivery of GapmeRs may not achieve therapeutic levels in the bulk tumor. It may require convection-enhanced delivery, as shown by Souweidane et al., The Lancet Oncology, 19(8), 1040-50 (2018). The inventors can also explore the option of a "cocktail GapmeR" targeting all three eRNAs at once to access the combinatory effect of these eRNAs on glioma stem cell samples. To explore the efficiency of eRNAs as glioma stem cell-specific therapy, the inventors can combine each eRNA with temozolomide (the current chemotherapy for Glioblastoma Multiforme) at various concentrations and then evaluate the effects on glioma stem cells.

Example 5

Identification of Glioma Stem Cell Specific eRNAs

Figure 7:
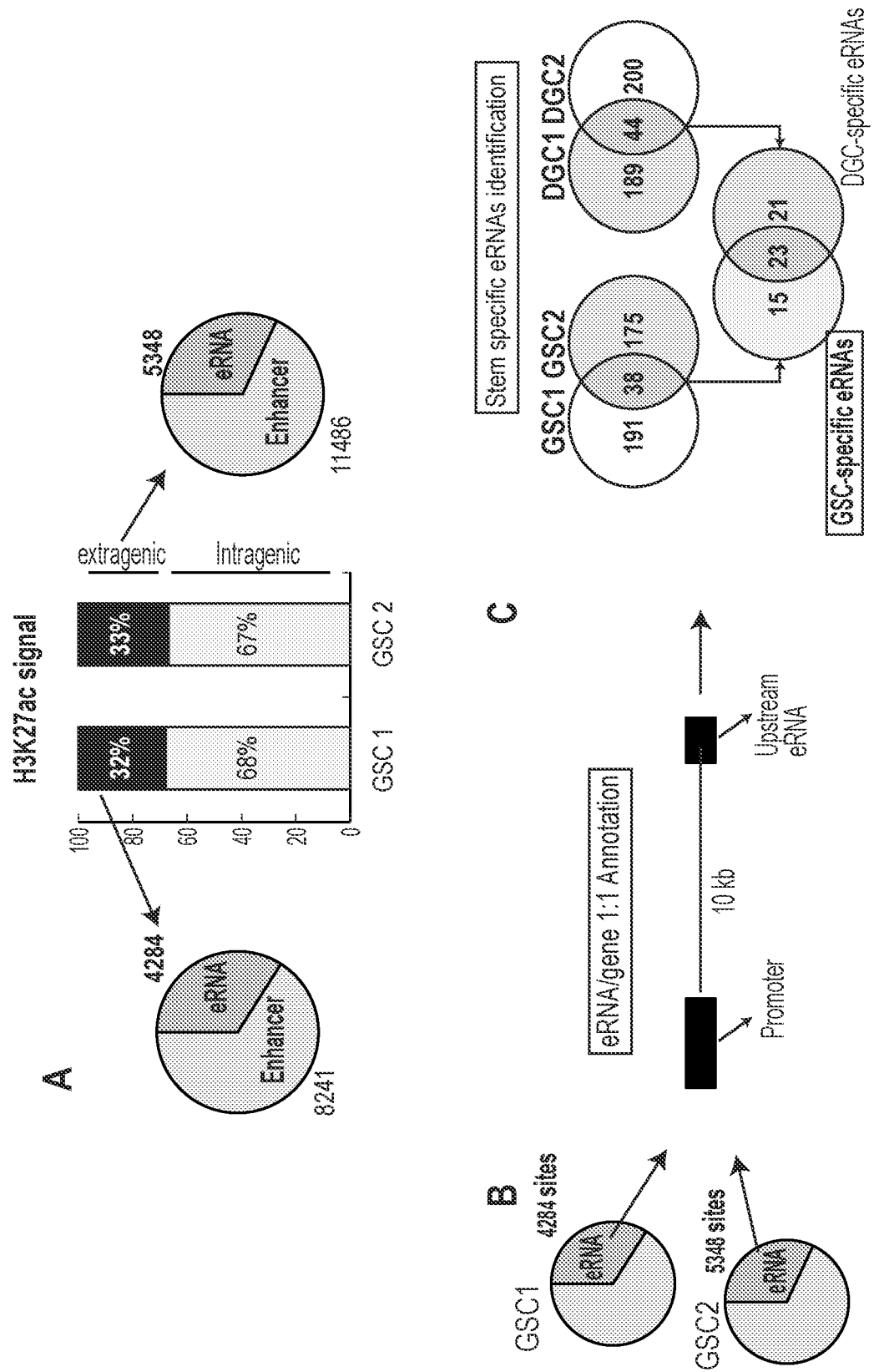
FIG. 7 is a set of pie charts showing the identification of glioma stem cell-specific eRNAs through a H3K27Ac and RNA Pol II ChIP-seq analysis pipeline. H3K27Ac and RNA Pol II peaks are overlapping the NINJ1 eRNA. H3K27Ac ChIP-seq identified 39,247 and 50,885 sites in GSC1 and GSC2 respectively. These sites were filtered for co-presence of RNA Pol II signal, which resulted in 4284 and 5348 putative eRNA sites in GSC1 and GSC2. See FIG. 7(A). These sites were filtered looking specifically at eRNA sites that have 1:1 relationship with a gene and are located within 10 kb upstream from an annotated promoter of a gene. See FIG. 7(B). This analysis resulted in 229 eRNAs for GSC1 and 213 eRNAs for GSC2. These eRNAs were compared with eRNAs detected (through the same analysis pipeline) in differentiated glioblastoma stromal cells and discovered fifteen glioma stem cell-specific eRNAs that are common in the two patients. See FIG. 7(C).

To identify glioma stem cell-specific eRNAs, the inventors performed H3K27Ac ChIP-seq and RNA PolII ChIP-seq on glioma stem cells and differentiated glioma cells from two patients. H3K27Ac is a histone mark that identifies active enhancers and RNA PolII denotes active transcription. Detection of overlapping peaks on the genome where H3K27Ac and RNA PolII are co-present is an indication of the presence of an eRNA. H3K27Ac ChIP-seq identified 39,247 and 50,885 sites in GSC1 and GSC2 respectively. These sites were filtered for co-presence of RNA Pol II signal, which resulted in 4284 and 5348 putative eRNA sites in GSC1 and GSC2. See FIG. 7(A). The inventors filtered these sites looking specifically at eRNA sites that have 1:1 relationship with a gene and are located within 10 kb upstream from an annotated promoter of a gene. See FIG. 7(B). This analysis resulted in 229 eRNAs for GSC1 and 213 eRNAs for GSC2. The inventors then compared these eRNAs with eRNAs detected (through the same analysis pipeline) in differentiated glioblastoma stromal cells and discovered fifteen glioma stem cell-specific eRNAs that are common in the two patients. See FIG. 7(C). The inventors visualized the presence of H3K27Ac and RNA Pol II signal on the enhancer region of NINJ1 gene, denoting the presence of NINJ1 eRNA in GSC1 and GSC2.

Example 6

Expression of eRNAs in Patients with Glioblastoma

Expression of eTMEM88b, eNINJ1 and eRTP5 (three of the fifteen GSC-specific eRNAs that most significantly correlate with patient survival) was examined in GSCs isolated from nine patients with glioblastoma and in two human neural stem cell lines (H9 and H4 derivatives from NIH) as controls. See FIG. 5. All patients express the three eRNAs in variable levels. eTMEM88b shows high expression in GSCs and control cells, eNINJ1 is expressed in moderate levels in GSCs and not detected in control cells, while eRTP5 is barely detected in GSCs or neural stem cells. See FIG. 8.

Figure 9:
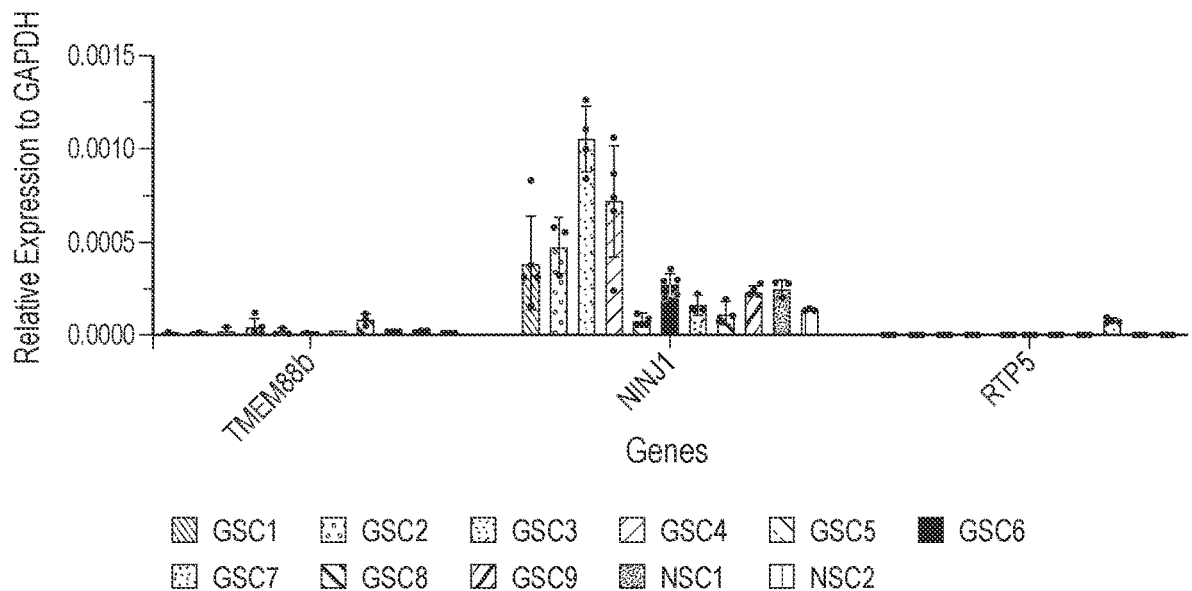
FIG. 9 is a bar graph showing the expression of TMEM88b, NINJ1, and RTP5 genes in nine patient-derived glioma stem cells and two human neural stem cell samples.

The inventors determined the expression of the cognate genes of the eRNAs in GSCs and control human neural stem cells, since eRNAs usually regulate the expression of their cognate genes. Ninj1 gene is expressed in variable levels in all nine GSC samples and in the two neural stem cell samples. TMEM88b shows little expression in two of the nine GSCs, while RTP5 is not expressed in GSCs. See FIG. 9. To determine the expression of the three eRNAs in glioblastoma tumors, the inventors performed Nanostring expression analysis in glioblastoma tumor samples from seventy patients that were operated in Rhode Island Hospital. This result showed that eNINJ1 and eTMEM88b have variable but high expression in all seventy glioblastoma tumor samples, while eRTP5 shows low expression. Clustering of eRNAs was determined using Euclidean distance.

The inventors correlated the tissue expression of the three eRNAs to survival of the patients using the standardized log-rank statistics and maximally selected rank statistic. Patients with high expression of eNINJ1 show the most significant correlation with decreased survival ($p<0.002$), while high expression of eTMEM88b and eRTP5 also correlated with decreased survival but the correlation was less significant than eNINJ1. See FIG. 5.

Example 7

Figure 10:
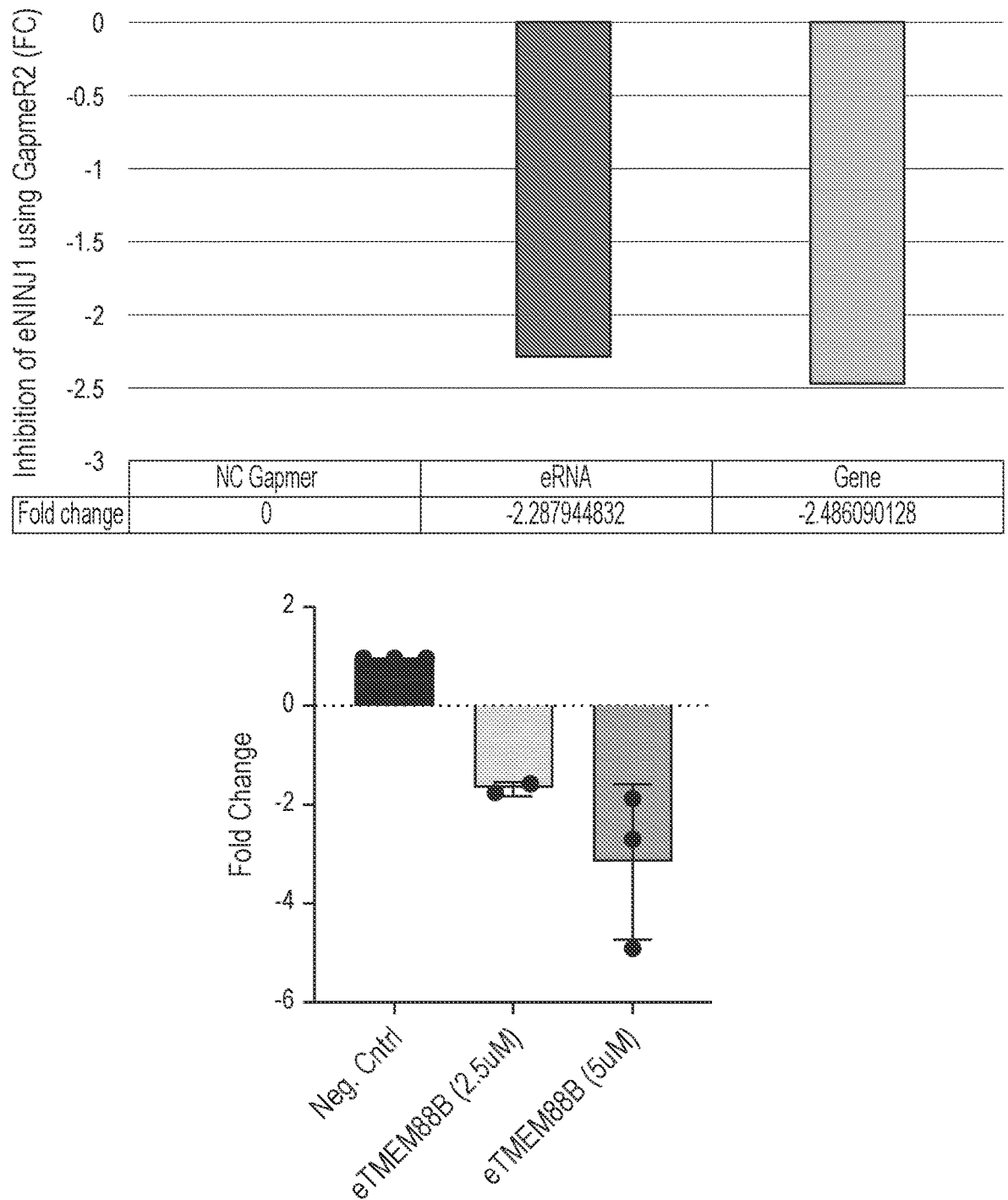
FIG. 10 is a pair of bar graphs showing the treatment of patient derived glioma stem cells with eNINJ1 and eTMEM88B targeting GapmeRs results in 50% inhibition of the eRNA expression. The assays were performed three independent times (n=3 biological replicates) in one patient's glioma stem cells.

Design and Synthesis of Oligonucleotide GapmeRs Targeting eNINJ1 and eTMEM88b The inventors designed LNA-modified oligonucleotide GapmeRs targeting various areas of the eNINJ1 and eTMEM88b sequence and tested them in patient-derived GSCs to verify inhibition of the eRNA expression. The initial candidate GapmeRs show significant inhibition of eNINJ1 and eTMEM88b expression, but only up to 50% of the total eRNA expression. See FIG. 10.

To increase GapmeR induced inhibition of the Ninj1 eRNA, the inventors designed ninety-six candidates GapmeRs spanning the entire sequence of the Ninj1 eRNA. See TABLE 1 for some of the sequences of the GapmeRs to be used in a high-throughput in vitro assay for discovering the best inhibitory GapmeR for further in vitro and in vivo studies as an eRNA therapeutic against eNinj1.

TABLE 1

| Name of enhancer RNA | Antisense LNA GapmeR sequence | SEQ ID NO: |
|---|---|---|
| eTMEM88B | 5'-CGGGAGTAGAAGTTGG-3' | 1 |
| eNINJ1 | 5'-GCGTCTAGGCTGGCAG-3' | 2 |

Example 8

Inhibition of eTMEM888 Results in Inhibition of Glioma Stem Cell Identity Genes.

Figure 11:
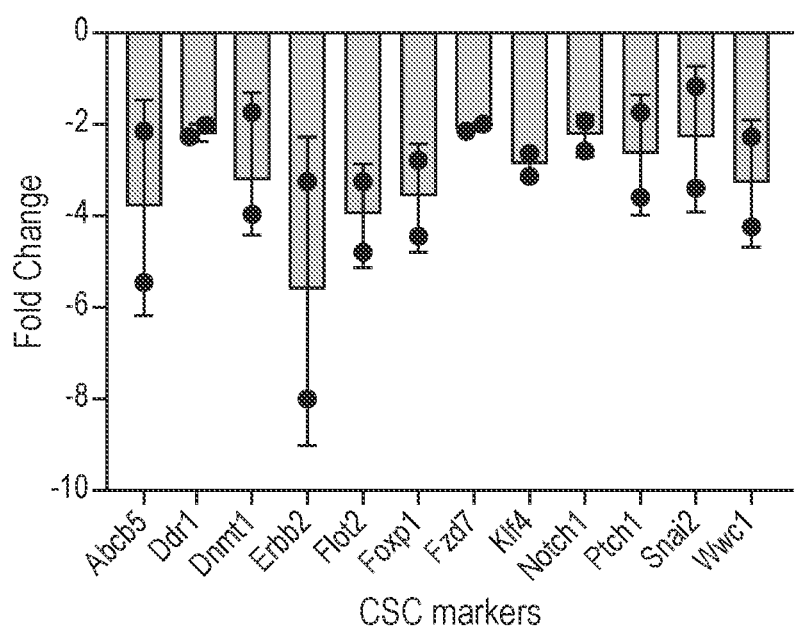
FIG. 11 is a bar graph showing the treatment of patient-derived glioma stem cells with 5 μM of the eTMEM88B GapmeR results in significant inhibition of cancer stem cell identity genes. The assay was performed two independent times (n=2 biological replicates).

The significance of these genes in glioblastoma has been shown previously. Notch1 regulates glioblastoma growth, resistance to apoptosis, and maintenance of GSC properties. Notch1 regulates expression of PTCH1, Sox2, and Nanog. Klf4 regulates growth of GSCs and is upregulated following treatment of glioblastoma with chemotherapy. Fold-change of these genes is calculated in comparison to GSCs treated with non-targeting GapmeRs and normalized to housekeeping gene expression. See FIG. 11.

SEQUENCE LISTING eTMEM88B: Chromosome 1 (GSC1-start: 1430292-GSC2-end: 1430960).
Length: 668nucleotides.
ATCTAGTACATCATATTGCCAGCAGGGCTCAGCCTGTGACCAGCAAGGTCTGGGCTCCGTCTGGG
GCCAGGGTCAAGGCTCATTCCGTGGCCTTGAGCACAGCCTGGTGTGTGGCTGGGTCGAGTCCAGC
AGAAGTCTCGGGGTTTTCCAGCCTCCATCCGAGTCCGGCTTTGATGCCTTTCCTGGTCAGACAGG
AGCCGGGCCAGTGGCCAAGCTGCCAGGATGGCTTCCCCGGGGCCGCGGCCGCCTTCCTTCCCCTC
CTGCCCGGGCTGGCTCTGGTCGCCACTAGGGGTTGAAGATGAGGGCTCTCCTGGGAAGCTCTTGG
CTGAGGATCCGCCTGGTCCCGGAGCCGTGAAAACAACAGCTGGGCCTGGTGGGGGTGGGAGGCT
GAGCGGAGAGGCCAGCTCCCTTGGCTGCTGGGCAGGGTCTTCTGTCCACAGCTGCCTCAGGCGGC
TGTTTCCAAAGGTGTTTCCAGCTTCCCAGGCCCACCCTGAGGCCCCGCACCGCCAGGGAGGTGGA
AGGCACGGAGCAGCGAAGCCCGGCCCCGGCCCCGGCCGCCCGACCAGCTCACAGAGGAACACCTG
TGGGGGGGCCTGTGGGCGGTTCACAGAGGGATGTAGGAACGTGCCTGTGGGAGGCCGTAGCCCCG
GAGACAGAGGCCTGGCC [SEQ ID NO: 3].

eRTP5: Chromosome 2 (GSC1-start: 242088593-GSC2-end: 242088884).
Length: 291 nucleotides.
CGGCAGCAACACTGCCACGCGAATCCGCGCCGGCCAATCAGCATGGCCAGGGGCGGGCTTCCCT
GAGGCGCGCCGAGAGGCGGTGGCCCACTTCCGGCAATAATCGCCTGGTCGCCGTCAGGTGCCGGC
CCAGGTGGCAGGCGCGCCCGTTGGGCACTGGGGGACGCGGGCGCGTCAGGTGAAGACTGGGGGCT
GCAGGCGCGCTAGGTAGGTACGGGGTGCCGCGGGCGCGTCAGGTGAAGACTGGGCGCCGCAGGCG
CCTTAGGTGAAGATTGGGGATCGCGGGCGCG [SEQ ID NO: 4].

eNINJ1: Chromosome 9 (GSC1-start: 93143058-GSC2-end: 93144787).
Length: 1,832 nucleotides.
agaattgcctgaaccaggggttggaggttgcagcgggtggaaattttgccactgcactccagcct
gggtgacagagtgagaccctgtctcaaagaaaaaaaaaaaaaagaTACATCATCTGGGACAATAAC
CTTGAAAAGCAGGGGTCCCAGACGACCTTATTTGCAGAGAATGCGACTGCAGACGGCAAGCAGGG
GGGCATGCCCTTCGCTCTCTGTCCTCTGCTCTTTGCCCCGGCCACTGTCGGCCTCATCTGAAGGC
CACCTGTGCCTCACGGTCTGAAAACGCTGGTTTCCACAGCTGCTTCTCCTTCCAAATTTCCCTGG
AGTCTTGCTTTGGTGGCGAACCTCTGGTTCTATTCCTTCCTTTTAACTGAAGCCTATAGGAAAAA
TTTGGAAGTTGAAATATGCCAGTCCAAGGAAGGTGGACGTGGAGTTCTGAGGGTGGGGGTGCTGC
CAGGGAAGTGGCACTGTGCAGGGGACCGCCCCTGGGACCCCCTGGTTCCTGTCAAGAGCAGGTAG
Gggctgggcgcggtggctcacgcctataatcccagcactttgggaggtcaaggagagtggatcac
ctaaggtcaggagttcaagaccagctgaccaacatggtgaaaccccgtctctactaaaaatacaa
aaattagctgggcgtggtggcaggcgcctataatcccaggtattcaggaggctgaggcaggagaa
tagcttgaaccaggaggcagaggttgcagtgagctgagatcgcaccactgcactccagcctggg
cgacagagcgagactctgtctacacacacacacacacacacacacagacacacacacacacacaGAT
CAGGTAGGATGTGAGGTGTGTCCTCATGGCCGGACATGGGTGGGTGGGGCCAAACAACCACAGG
GACTCGTCCTGTGGCCACTGCTGCTCAGGAAGTGGATCCCAAGGAGCAGAGTCGCCAGACCCCTC
AGTTCCCAGCTCCACATTTAAGGCAGGTCTGGCCATGAGCCAGGCCTCTGCATGTGACCTGGGGC
CTCACTGTGGCATGGCTGCCTGTCCCACCTGTGGATGTTGCCTGTGCTGTGTAGAAGCCACATAG
CCTCCGGGGCGGCTCCCCAGAATGCCACATTTCCTGTCTCTGGCTCTGATGGCGTCTAGGCTGGC
AGGGGTCCCGGCCCCAGCAGTACTGTTGCCGGGCAGAGCTCAGGGCCACGTGCAGTTGGGTCTGG
CTGAGAGCATCTCATGGGTTTATGAGAACCCTTCCAGCACAAAGGGGCATTTATCAGGCAGGGAT
GGCATGTCTTGGTCTGAACACAGGAAACACAGAAATAGCCTTTCACAGAGTGCCAGCAGGGCTGG
GCTCGCCTGCTGTGGAGGGTGTCGGCTTTCCAACTCCTTCTCCAAGCTGTGCGACCCGTCCATGT
TCCCCTGTGAGTTGTTCTGTCCCAGACAGGGCATTCCCTGAGAACGCTCCTGCTGCAACTGgagg
gagagaggcagggagggaaagggggaagacttgcagggagaaggaagaagggagacagatggaga -continued

SEQUENCE LISTING

```
cagacagaaggagggatggaagaaatgagagagagagagggagggagaTGGAAACATAGATTGTC
TCCACTGTGACACCCTGCCTCCATGGTTCTCCATGATGGGAATGGAATTCATGTCTCACCTGGCA
GCAAGGGTCTCCACAATATGACTTCACCTTCTTTCTCTTAGTAAGGCGAGAGCAGACAGGCAGAC
ACTCCAGGAAGTAACTGATGTGTCCCTGAAAATGCCTGTCTTTCCCAGCTTGTACAACTTTGCTT
GTGTTATTTCTT [SEQ ID NO: 5].
```

The following sequences were generated using bioinformatics methods whereby the target eRNA sequence (eN-INJ1) a 1,832 nt non-coding RNA was screened to find ideal/target regions that were 20 nucleotides long. The ideal/target regions were selected using criteria such as % GC content (~30-60%), number of miRNA hits (score of was selected); Gene hits (scores of 1 or less were selected) and a rank system (this showed whether a target sequence was good or not; bioinformatics stuff really). The top (50) target regions were selected to synthesize and generate GapmeRs (LNA and 2'MOE) that target the selected regions of eNINJ1. (lN)# is a LNA nucleotide. (eN)# is a 2'MOE nucleotide. (dN)# is a deoxyribonucleotide (DNA).

LNCRNA_22_LNA. Target 20 nucleotides (nt) (5'-3') contains the original eRNA sequence that was selected for GapmeR design (20 nucleotides each). UGUACAAGCUGGGAAAGACA [SEQ ID NO: 6].

LNCRNA_22_LNA. AS sequence (5'-3') contains the antisense sequence that targets the eRNA region above. The antisense sequences are provided as RNA nucleotides. UGUCUUUCCCAGCUUGUACA [SEQ ID NO: 7].

LNCRNA_22_LNA. 5-10-5 LNA GapmeR contains LNA GapmeR sequences in this structural order: (5) LNA sequences followed by (10) DNA sequences and finally (5) LNA sequences. (lT)#(lG)#(lT)#(lC)#(lT)#(dT)#(dT)#(dC)#(dC)#(dC)#(dA) #(dG)#(dC)#(dT)#(dT)#(lG)#(lT)#(lA)#(lC)#(lA) [SEQ ID NO: 8].

LNCRNA_22_LNA. 5-10-5 MOE GapmeR contains 2' MOE GapmeR sequences in this structural order: (5) 2'MOE sequences followed by (10) DNA sequences and finally (5) 2'MOE sequences. (eT)#(eG)#(eT)#(eC)#(eT)#(dT)#(dT)#(dC) #(dC)#(dC)#(dA)#(dG)#(dC)#(dT)#(dT)#(eG)#(eT)#(eA)#(eC)#(eA) [SEQ ID NO: 9].

LNCRNA_LNA. Target 20 nt (5'-3') contains the original eRNA sequence that was selected for GapmeR design (20 nucleotides each). CUGGGAAAGACAGGCAUUUU [SEQ ID NO: 10].

LNCRNA_30_LNA. AS sequence (5'-3') contains the antisense sequence that targets the eRNA region above. The antisense sequences are provided as RNA nucleotides. AAAAUGCCUGUCUUUCCCAG [SEQ ID NO: 11].

LNCRNA_30_LNA. 5-10-5 LNA GapmeR contains LNA GapmeR sequences in this structural order: (5) LNA sequences followed by (10) DNA sequences and finally (5) LNA sequences. (lA)#(lA)#(lA)#(lA)#(lT)#(dG)#(dC)#(dC)#(dT)#(dG)#(dT) #(dC)#(dT)#(dT)#(dT)#(lC)#(lC)#(lC)#(lA)#(lG) [SEQ ID NO: 12].

LNCRNA_30_LNA. 5-10-5 MOE GapmeR contains 2'MOE GapmeR sequences in this structural order: (5) 2'MOE sequences followed by (10) DNA sequences and finally (5) 2'MOE sequences. (eA)#(eA)#(eA)#(eA)#(eT)#(dG)#(dC) #(dC)#(dT)#(dG)#(dT)#(dC)#(dT)#(dT)#(dT)#(eC)#(eC)#(eC)#(eA)#(eG) [SEQ ID NO: 13].

LNCRNA_40_LNA. Target 20 nt (5'-3') contains the original eRNA sequence that was selected for GapmeR design (20 nucleotides each). CAGGCAUUUUCAGGGACACA [SEQ ID NO: 14].

LNCRNA_40_LNA. AS sequence (5'-3') contains the antisense sequence that targets the eRNA region above. The antisense sequences are provided as RNA nucleotides. UGUGUCCCUGAAAAUGCCUG [SEQ ID NO: 15].

LNCRNA_40_LNA. 5-10-5 LNA GapmeR contains LNA GapmeR sequences in this structural order: (5) LNA sequences followed by (10) DNA sequences and finally (5) LNA sequences. (lT)#(lG)#(lT)#(lG)#(lT)#(dC)#(dC)#(dC) #(dT)#(dG)#(dA) #(dA)#(dA)#(dA)#(dT)#(lG)#(lC)#(lC)#(lT)#(lG) [SEQ ID NO: 16].

LNCRNA_40_LNA. 5-10-5 MOE GapmeR contains 2'MOE GapmeR sequences in this structural order: (5) 2'MOE sequences followed by (10) DNA sequences and finally (5) 2'MOE sequences. (eT)#(eG)#(eT)#(eG)#(eT)# (dC)#(dC) #(dC)#(dT)#(dG)#(dA)#(dA)#(dA)#(dA)#(dT)#(eG)#(eC)#(eC)#(eT)#(eG) [SEQ ID NO: 18].

LNCRNA_49_LNA. Target 20 nt (5'-3') contains the original eRNA sequence that was selected for GapmeR design (20 nucleotides each). UCAGGGACACAUCAGUUACU [SEQ ID NO: 19].

LNCRNA_49_LNA. AS sequence (5'-3') contains the antisense sequence that targets the eRNA region above. The antisense sequences are provided as RNA nucleotides. AGUAACUGAUGUGUCCCUGA [SEQ ID NO: 20].

LNCRNA_49_LNA. 5-10-5 LNA GapmeR contains LNA GapmeR sequences in this structural order: (5) LNA sequences followed by (10) DNA sequences and finally (5) LNA sequences. (lA)#(lG)#(lT)#(lA)#(lA)#(dC)#(dT)#(dG) #(dA)#(dT)#(dG) #(dT)#(dG)#(dT)#(dC)#(lC)#(lC)#(lT)#(lG)#(lA) [SEQ ID NO: 21].

LNCRNA_49_LNA. 5-10-5 MOE GapmeR contains 2'MOE GapmeR sequences in this structural order: (5) 2'MOE sequences followed by (10) DNA sequences and finally (5) 2'MOE sequences. (eA)#(eG)#(eT)#(eA)#(eA)# (dC)#(dT) #(dG)#(dA)#(dT)#(dG)#(dT)#(dG)#(dT)#(dC)#(eC)#(eC)#(eT)#(eG)#(eA) [SEQ ID NO: 22].

LNCRNA_51_LNA. Target 20 nt (5'-3') contains the original eRNA sequence that was selected for GapmeR design (20 nucleotides each). AGGGACACAUCAGUUACUUC [SEQ ID NO: 23].

LNCRNA_51_LNA. AS sequence (5'-3') contains the antisense sequence that targets the eRNA region above. The antisense sequences are provided as RNA nucleotides. GAAGUAACUGAUGUGUCCCU [SEQ ID NO: 24].

LNCRNA_51_LNA. 5-10-5 LNA GapmeR contains LNA GapmeR sequences in this structural order: (5) LNA sequences followed by (10) DNA sequences and finally (5) LNA sequences. (lG)#(lA)#(lA)#(lG)#(lT)#(dA)#(dA)# (dC)#(dT)#(dG)#(dA) #(dT)#(dG)#(dT)#(dG)#(lT)#(lC)#(lC)#(lC)#(lT) [SEQ ID NO: 25].

LNCRNA_51_LNA. 5-10-5 MOE GapmeR contains 2'MOE GapmeR sequences in this structural order: (5) 2'MOE sequences followed by (10) DNA sequences and finally (5) 2'MOE sequences. (eG)#(eA)#(eA)#(eG)#(eT)# (dA)#(dA) #(dC)#(dT)#(dG)#(dA)#(dT)#(dG)#(dT)#(dG)# (eT)#(eC)#(eC)#(eC)#(eT) [SEQ ID NO: 26].

LNCRNA_109_LNA. Target 20 nt (5'-3') contains the original eRNA sequence that was selected for GapmeR design (20 nucleotides each). AAAGAAGGUGAAGU-CAUAUU [SEQ ID NO: 27].

LNCRNA_109_LNA. AS sequence (5'-3') contains the antisense sequence that targets the eRNA region above. The antisense sequences are provided as RNA nucleotides. AAUAUGACUUCACCUUCUUU [SEQ ID NO: 28].

LNCRNA_109_LNA. 5-10-5 LNA GapmeR contains LNA GapmeR sequences in this structural order: (5) LNA sequences followed by (10) DNA sequences and finally (5) LNA sequences. (lA)#(lA)#(lT)#(lA)#(lT)#(dG)#(dA)#(dC)#(dT)#(dT)#(dC) #(dA)#(dC)#(dC)#(dT)#(lT)#(lC)#(lT)#(lT)#(lT) [SEQ ID NO: 29].

LNCRNA_109_LNA. 5-10-5 MOE GapmeR contains 2' MOE GapmeR sequences in this structural order: (5) 2'MOE sequences followed by (10) DNA sequences and finally (5) 2'MOE sequences. (eA)#(eA)#(eT)#(eA)#(eT)#(dG)#(dA)#(dC) #(dT)#(dT)#(dC)#(dA)#(dC)#(dC)#(dT)#(eT)#(eC)#(eT)#(eT)#(eT) [SEQ ID NO: 30].

LNCRNA_118_LNA. Target 20 nt (5'-3') contains the original eRNA sequence that was selected for GapmeR design (20 nucleotides each). GAAGUCAUAUUGUGGA-GACC [SEQ ID NO: 31].

LNCRNA_118_LNA. AS sequence (5'-3') contains the antisense sequence that targets the eRNA region above. The antisense sequences are provided as RNA nucleotides. GGUCUCCACAAUAUGACUUC [SEQ ID NO: 32].

LNCRNA_118_LNA. 5-10-5 LNA GapmeR contains LNA GapmeR sequences in this structural order: (5) LNA sequences followed by (10) DNA sequences and finally (5) LNA sequences. (lG)#(lG)#(lT)#(lC)#(lT)#(dC)#(dC)#(dA)#(dC)#(dA)#(dA) #(dT)#(dA)#(dT)#(dG)#(lA)#(lC)#(lT)#(lT)#(lC) [SEQ ID NO: 33].

LNCRNA_118_LNA. 5-10-5 MOE GapmeR contains 2'MOE GapmeR sequences in this structural order: (5) 2'MOE sequences followed by (10) DNA sequences and finally (5) 2'MOE sequences. (eG)#(eG)#(eT)#(eC)#(eT)#(dC)#(dC)#(dA) #(dC)#(dA)#(dA)#(dT)#(dA)#(dT)#(dG)#(eA)#(eC)#(eT)#(eT)#(eC) [SEQ ID NO: 34].

LNCRNA_141_LNA. Target 20 nt (5'-3') contains the original eRNA sequence that was selected for GapmeR design (20 nucleotides each). GCUGCCAGGUGAGA-CAUGAA [SEQ ID NO: 35].

LNCRNA_141_LNA. AS sequence (5'-3') contains the antisense sequence that targets the eRNA region above. The antisense sequences are provided as RNA nucleotides. UUCAUGUCUCACCUGGCAGC [SEQ ID NO: 36].

LNCRNA_141_LNA. 5-10-5 LNA GapmeR contains LNA GapmeR sequences in this structural order: (5) LNA sequences followed by (10) DNA sequences and finally (5) LNA sequences. (lT)#(lT)#(lC)#(lA)#(lT)#(dG)#(dT)#(dC)#(dT) #(dC)#(dA)#(dC)#(dC)#(dT)#(dG)#(lG)#(lC)#(lA)#(lG)#(lC) [SEQ ID NO: 37].

LNCRNA_141_ LNA. 5-10-5 MOE GapmeR contains 2'MOE GapmeR sequences in this structural order: (5) 2'MOE sequences followed by (10) DNA sequences and finally (5) 2'MOE sequences. (eT)#(eT)#(eC)#(eA)#(eT)#(dG)#(dT)#(dC) #(dT)#(dC)#(dA)#(dC)#(dC)#(dT)#(dG)#(eG)#(eC)#(eA)#(eG)#(eC) [SEQ ID NO: 38].

LNCRNA_150_LNA. Target 20 nt (5'-3') contains the original eRNA sequence that was selected for GapmeR design (20 nucleotides each). UGAGACAUGAAUUC-CAUUCC [SEQ ID NO: 39].

LNCRNA_150_LNA. AS sequence (5'-3') contains the antisense sequence that targets the eRNA region above. The antisense sequences are provided as RNA nucleotides. GGAAUGGAAUUCAUGUCUCA [SEQ ID NO: 40].

LNCRNA_150_LNA. 5-10-5 LNA GapmeR contains LNA GapmeR sequences in this structural order: (5) LNA sequences followed by (10) DNA sequences and finally (5) LNA sequences. (lG)#(lG)#(lA)#(lA)#(lT)#(dG)#(dG)#(dA)#(dA)#(dT)#(dT) #(dC)#(dA)#(dT)#(dG)#(lT)#(lC)#(lT)#(lC)#(lA) [SEQ ID NO: 41].

LNCRNA_150_LNA. 5-10-5 MOE GapmeR contains 2'MOE GapmeR sequences in this structural order: (5) 2'MOE sequences followed by (10) DNA sequences and finally (5) 2'MOE sequences. (eG)#(eG)#(eA)#(eA)(eT)#(dG)#(dG) #(dA)#(dA)#(dT)#(dT)#(dC)#(dA)#(dT)#(dG)#(eT)#(eC)#(eT)#(eC)#(eA) [SEQ ID NO: 42].

LNCRNA_196_LNA. Target 20 nt (5'-3') contains the original eRNA sequence that was selected for GapmeR design (20 nucleotides each). UGUCACAGUGGA-GACAAUCU [SEQ ID NO: 43].

LNCRNA_196_LNA. AS sequence (5'-3') contains the antisense sequence that targets the eRNA region above. The antisense sequences are provided as RNA nucleotides. AGAUUGUCUCCACUGUGACA [SEQ ID NO: 44].

LNCRNA_196_LNA. 5-10-5 LNA GapmeR contains LNA GapmeR sequences in this structural order: (5) LNA sequences followed by (10) DNA sequences and finally (5) LNA sequences. (lA)#(lG)#(lA)#(lT)#(lT)#(dG)#(dT)#(dC) #(dT)#(dC)#(dC) #(dA)#(dC)#(dT)#(dG)#(lT)#(lG)#(lA)#(lC)#(lA) [SEQ ID NO: 45].

LNCRNA_196_LNA. 5-10-5 MOE GapmeR contains 2' MOE GapmeR sequences in this structural order: (5) 2'MOE sequences followed by (10) DNA sequences and finally (5) 2'MOE sequences. (eA)#(eG)#(eA)#(eT)#(eT)#(dG)#(dT) #(dC)#(dT)#(dC)#(dC)#(dA)#(dC)#(dT)#(dG)#(eT)#(eG)#(eA)#(eC)#(eA) [SEQ ID NO: 46].

LNCRNA_250_LNA. Target 20 nt (5'-3') contains the original eRNA sequence that was selected for GapmeR design (20 nucleotides each). UCUUCCAUCCCUCC-UUCUGU [SEQ ID NO: 47].

LNCRNA_250_LNA. AS sequence (5'-3') contains the antisense sequence that targets the eRNA region above. The antisense sequences are provided as RNA nucleotides. ACAGAAGGAGGGAUGGAAGA [SEQ ID NO: 48].

LNCRNA_250_LNA. 5-10-5 LNA GapmeR contains LNA GapmeR sequences in this structural order: (5) LNA sequences followed by (10) DNA sequences and finally (5) LNA sequences. (lA)#(lC)#(lA)#(lG)#(lA)#(dA)#(dG)#(dG)#(dA)#(dG)#(dG) #(dG)#(dA)#(dT)#(dG)#(lG)#(lA)#(lA)#(lG)#(lA) [SEQ ID NO: 49].

LNCRNA_250_LNA. 5-10-5 MOE GapmeR contains 2' MOE GapmeR sequences in this structural order: (5) 2'MOE sequences followed by (10) DNA sequences and finally (5) 2'MOE sequences. (eA)#(eC)#(eA)#(eG)#(eA)#(dA)#(dG) #(dG)#(dA)#(dG)#(dG)#(dG)#(dA)#(dT)#(dG)#(eG)#(eA)#(eA)#(eG)#(eA) [SEQ ID NO: 50].

LNCRNA_377_LNA. Target 20 nt (5'-3') contains the original eRNA sequence that was selected for GapmeR design (20 nucleotides each). UCUGGGACAGAACAA-CUCAC [SEQ ID NO: 51].

LNCRNA_377_LNA. AS sequence (5'-3') contains the antisense sequence that targets the eRNA region above. The antisense sequences are provided as RNA nucleotides. GUGAGUUGUUCUGUCCCAGA [SEQ ID NO: 52].

LNCRNA_377_LNA. 5-10-5 LNA GapmeR contains LNA GapmeR sequences in this structural order: (5) LNA sequences followed by (10) DNA sequences and finally (5)

LNA sequences. (lG)#(lT)#(lG)#(lA)#(lG)(dT)#(dT)#(dG)# (dT)#(dT)#(dC) #(dT)#(dG)#(dT)#(dC)#(lC)#(lC)#(lA)# (lG)#(lA) [SEQ ID NO: 53].

LNCRNA_377_LNA. 5-10-5 MOE GapmeR contains 2'MOE GapmeR sequences in this structural order: (5) 2'MOE sequences followed by (10) DNA sequences and finally (5) 2'MOE sequences. (eG)#(eT)#(eG)#(eA)#(eG) (dT)#(dT)#(dG) #(dT)#(dT)#(dC)#(dT)#(dG)#(dT)#(dC)# (eC)#(eC)#(eA)#(eG)#(eA) [SEQ ID NO: 54].

LNCRNA_485_LNA. Target 20 nt (5'-3') contains the original eRNA sequence that was selected for GapmeR design (20 nucleotides each). CUGUGAAAGGC-UAUUUCUGU [SEQ ID NO: 55].

LNCRNA_485_LNA. AS sequence (5'-3') contains the antisense sequence that targets the eRNA region above. The antisense sequences are provided as RNA nucleotides. ACAGAAAUAGCCUUUCACAG [SEQ ID NO: 56].

LNCRNA_485_LNA. 5-10-5 LNA GapmeR contains LNA GapmeR sequences in this structural order: (5) LNA sequences followed by (10) DNA sequences and finally (5) LNA sequences. (lA)#(lC)#(lA)#(lG)#(lA)#(dA)#(dA)# (dT)#(dA)#(dG)#(dC) #(dC)#(dT)#(dT)#(dT)#(lC)#(lA)# (lC)#(lA)#(lG) [SEQ ID NO: 57].

LNCRNA_485_LNA. 5-10-5 MOE GapmeR contains 2' MOE GapmeR sequences in this structural order: (5) 2'MOE sequences followed by (10) DNA sequences and finally (5) 2'MOE sequences. (eA)#(eC)#(eA)#(eG)#(eA)#(dA)#(dA)# #(dT)#(dA)#(dG)#(dC)#(dC)#(dT)#(dT)#(dT)#(eC)#(eA)# (eC)#(eA)#(eG) [SEQ ID NO: 58].

LNCRNA_491_LNA. Target 20 nt (5'-3') contains the original eRNA sequence that was selected for GapmeR design (20 nucleotides each). AAGGCUAUUUCUGU-GUUUCC [SEQ ID NO: 59].

LNCRNA_491_LNA. AS sequence (5'-3') contains the antisense sequence that targets the eRNA region above. The antisense sequences are provided as RNA nucleotides. GGAAACACAGAAAUAGCCUU [SEQ ID NO: 60].

LNCRNA_491_LNA. 5-10-5 LNA GapmeR contains LNA GapmeR sequences in this structural order: (5) LNA sequences followed by (10) DNA sequences and finally (5) LNA sequences. (lG)#(lG)#(lA)#(lA)#(lA)#(dC)#(dA)# (dC)#(dA)#(dG)#(dA) #(dA)#(dA)#(dT)#(dA)#(lG)#(lC)# (lC)#(lT)#(lT) [SEQ ID NO: 61].

LNCRNA_491_LNA. 5-10-5 MOE GapmeR contains 2'MOE GapmeR sequences in this structural order: (5) 2'MOE sequences followed by (10) DNA sequences and finally (5) 2'MOE sequences. (eG)#(eG)#(eA)#(eA)#(eA)# (dC)#(dA) #(dC)#(dA)#(dG)#(dA)#(dA)#(dA)#(dT)#(dA)# (eG)#(eC)#(eC)#(eT)#(eT) [SEQ ID NO: 62].

LNCRNA_499_LNA. Target 20 nt (5'-3') contains the original eRNA sequence that was selected for GapmeR design (20 nucleotides each). UUCUGUGUUUCCUGU-GUUCA [SEQ ID NO: 63].

LNCRNA_499_LNA. AS sequence (5'-3') contains the antisense sequence that targets the eRNA region above. The antisense sequences are provided as RNA nucleotides. UGAACACAGGAAACACAGAA [SEQ ID NO: 64].

LNCRNA_499_LNA. 5-10-5 LNA GapmeR contains LNA GapmeR sequences in this structural order: (5) LNA sequences followed by (10) DNA sequences and finally (5) LNA sequences. (lT)#(lG)#(lA)#(lA)#(lC)#(dA)#(dC)#(dA)# (dG)#(dG)#(dA) #(dA)#(dA)#(dC)#(dA)#(lC)#(lA)#(lG)# (lA)#(lA) [SEQ ID NO: 65].

LNCRNA_499_LNA. 5-10-5 MOE GapmeR contains 2' MOE GapmeR sequences in this structural order: (5) 2'MOE sequences followed by (10) DNA sequences and finally (5) 2'MOE sequences. (eT)#(eG)#(eA)#(eA)#(eC)#(dA)#(dC) #(dA)#(dG)#(dG)#(dA)#(dA)#(dA)#(dC)#(dA)#(eC)#(eA) #(eG)#(eA)#(eA) [SEQ ID NO: 66].

LNCRNA_500_LNA. Target 20 nt (5'-3') contains the original eRNA sequence that was selected for GapmeR design (20 nucleotides each). UCUGUGUUUCCUGU-GUUCAG [SEQ ID NO: 67].

LNCRNA_500_LNA. AS sequence (5'-3') contains the antisense sequence that targets the eRNA region above. The antisense sequences are provided as RNA nucleotides. CUGAACACAGGAAACACAGA [SEQ ID NO: 68].

LNCRNA_500_LNA. 5-10-5 LNA GapmeR contains LNA GapmeR sequences in this structural order: (5) LNA sequences followed by (10) DNA sequences and finally (5) LNA sequences. (lC)#(lT)#(lG)#(lA)#(lA)#(dC)#(dA)#(dC) #(dA)#(dG)#(dG) #(dA)#(dA)#(dA)#(dC)#(lA)#(lC)#(lA)# (lG)#(lA) [SEQ ID NO: 69].

LNCRNA_500_LNA. 5-10-5 MOE GapmeR contains 2'MOE GapmeR sequences in this structural order: (5) 2'MOE sequences followed by (10) DNA sequences and finally (5) 2'MOE sequences. (eC)#(eT)#(eG)#(eA)#(eA)# (dC)#(dA) #(dC)#(dA)#(dG)#(dG)#(dA)#(dA)#(dA)#(dC)# (eA)#(eC)#(eA)#(eG)#(eA) [SEQ ID NO: 70].

LNCRNA_517_LNA. Target 20 nt (5'-3') contains the original eRNA sequence that was selected for GapmeR design (20 nucleotides each). CAGACCAAGACAUGC-CAUCC [SEQ ID NO: 71].

LNCRNA_517_LNA. AS sequence (5'-3') contains the antisense sequence that targets the eRNA region above. The antisense sequences are provided as RNA nucleotides. GGAUGGCAUGUCUUGGUCUG [SEQ ID NO: 72].

LNCRNA_517_LNA. 5-10-5 LNA GapmeR contains LNA GapmeR sequences in this structural order: (5) LNA sequences followed by (10) DNA sequences and finally (5) LNA sequences. (lG)#(lG)#(lA)#(lT)#(lG)#(dG)#(dC)# (dA)#(dT)#(dG)#(dT) #(dC)#(dT)#(dT)#(dG)#(lG)#(lT)# (lC)#(lT)#(lG) [SEQ ID NO: 73].

LNCRNA_517_LNA. 5-10-5 MOE GapmeR contains 2'MOE GapmeR sequences in this structural order: (5) 2'MOE sequences followed by (10) DNA sequences and finally (5) 2'MOE sequences. (eG)#(eG)#(eA)#(eT)#(eG)# (dG)#(dC) #(dA)#(dT)#(dG)#(dT)#(dC)#(dT)#(dT)#(dG)# (eG)#(eT)#(eC)#(eT)#(eG) [SEQ ID NO: 74].

LNCRNA_527_LNA. Target 20 nt (5'-3') contains the original eRNA sequence that was selected for GapmeR design (20 nucleotides each). CAUGCCAUCCCUGC-CUGAUA [SEQ ID NO: 75].

LNCRNA_527_LNA. AS sequence (5'-3') contains the antisense sequence that targets the eRNA region above. The antisense sequences are provided as RNA nucleotides. UAUCAGGCAGGGAUGGCAUG [SEQ ID NO: 76].

LNCRNA_527_LNA. 5-10-5 LNA GapmeR contains LNA GapmeR sequences in this structural order: (5) LNA sequences followed by (10) DNA sequences and finally (5) LNA sequences. (lT)#(lA)#(lT)#(lC)#(lA)#(dG)#(dG)#(dC) #(dA)#(dG)#(dG) #(dG)#(dA)#(dT)#(dG)#(lG)#(lC)#(lA)# (lT)#(lG) [SEQ ID NO: 77].

LNCRNA_527_LNA. 5-10-5 MOE GapmeR contains 2'MOE GapmeR sequences in this structural order: (5) 2'MOE sequences followed by (10) DNA sequences and finally (5) 2'MOE sequences. (eT)#(eA)#(eT)#(eC)#(eA)# (dG)#(dG) #(dC)#(dA)#(dG)#(dG)#(dG)#(dA)#(dT)#(dG)# (eG)#(eC)#(eA)#(eT)#(eG) [SEQ ID NO: 78].

LNCRNA_536_LNA. Target 20 nt (5'-3') contains the original eRNA sequence that was selected for GapmeR design (20 nucleotides each). CCUGC-CUGAUAAAUGCCCCU [SEQ ID NO: 79].

LNCRNA_536_LNA. AS sequence (5'-3') contains the antisense sequence that targets the eRNA region above. The antisense sequences are provided as RNA nucleotides. AGGGGCAUUUAUCAGGCAGG [SEQ ID NO: 80].

LNCRNA_536_LNA. 5-10-5 LNA GapmeR contains LNA GapmeR sequences in this structural order: (5) LNA sequences followed by (10) DNA sequences and finally (5) LNA sequences. (lA)#(lG)#(lG)#(lG)#(lG)#(dC)#(dA)#(dT)#(dT)#(dT)#(dA) #(dT)#(dC)#(dA)#(dG)#(lG)#(lC)#(lA)#(lG)#(lG) [SEQ ID NO: 81].

LNCRNA_536_LNA. 5-10-5 MOE GapmeR contains 2'MOE GapmeR sequences in this structural order: (5) 2'MOE sequences followed by (10) DNA sequences and finally (5) 2'MOE sequences. (eA)#(eG)#(eG)#(eG)#(eG)#(dC)#(dA) #(dT)#(dT)#(dT)#(dA)#(dT)#(dC)#(dA)#(dG)#(eG)#(eC)#(eA)#(eG)#(eG) [SEQ ID NO: 82].

LNCRNA_555_LNA. Target 20 nt (5'-3') contains the original eRNA sequence that was selected for GapmeR design (20 nucleotides each). UUUGUGCUGGAAGGGUUCUC [SEQ ID NO: 83].

LNCRNA_555_LNA. AS sequence (5'-3') contains the antisense sequence that targets the eRNA region above. The antisense sequences are provided as RNA nucleotides. GAGAACCCUUCCAGCACAAA [SEQ ID NO: 84].

LNCRNA_555_LNA. 5-10-5 LNA GapmeR contains LNA GapmeR sequences in this structural order: (5) LNA sequences followed by (10) DNA sequences and finally (5) LNA sequences. (lG)#(lA)#(lG)#(lA)#(lA)#(dC)#(dC)#(dC)#(dT)#(dT)#(dC) #(dC)#(dA)#(dG)#(dC)#(lA)#(lC)#(lA)#(lA)#(lA) [SEQ ID NO: 85].

LNCRNA_555_LNA. 5-10-5 MOE Gapmer contains 2'MOE GapmeR sequences in this structural order: (5) 2'MOE sequences followed by (10) DNA sequences and finally (5) 2'MOE sequences. (eG)#(eA)#(eG)#(eA)#(eA)#(dC)#(dC) #(dC)#(dT)#(dT)#(dC)#(dC)#(dA)#(dG)#(dC)#(eA)#(eC)#(eA)#(eA)#(eA) [SEQ ID NO: 86].

LNCRNA_556_LNA. Target 20 nt (5'-3') contains the original eRNA sequence that was selected for GapmeR design (20 nucleotides each). UUGUGCUGGAAGGGUUCUCA [SEQ ID NO: 87].

LNCRNA_556_LNA. AS sequence (5'-3') contains the antisense sequence that targets the eRNA region above. The antisense sequences are provided as RNA nucleotides. UGAGAACCCUUCCAGCACAA [SEQ ID NO: 88].

LNCRNA_556_LNA. 5-10-5 LNA GapmeR contains LNA GapmeR sequences in this structural order: (5) LNA sequences followed by (10) DNA sequences and finally (5) LNA sequences. (lT)#(lG)#(lA)#(lG)#(lA)#(dA)#(dC)#(dC)#(dC)#(dT)#(dT)#(dC)#(dC)#(dA)#(dG)#(lC)#(lA)#(lC)#(lA)#(lA) [SEQ ID NO: 89].

LNCRNA_556_LNA. 5-10-5 MOE GapmeR contains 2' MOE GapmeR sequences in this structural order: (5) 2'MOE sequences followed by (10) DNA sequences and finally (5) 2'MOE sequences. (eT)#(eG)#(eA)#(eG)#(eA)#(dA)#(dC)#(dC)#(dC)#(dT)#(dT)#(dC)#(dC)#(dA)#(dG)#(eC)#(eA)#(eC)#(eA)#(eA) [SEQ ID NO: 90].

LNCRNA_569_LNA. Target 20 nt (5'-3') contains the original eRNA sequence that was selected for GapmeR design (20 nucleotides each). GUUCUCAUAAACCCAUGAGA [SEQ ID NO: 91].

LNCRNA_569_LNA. AS sequence (5'-3') contains the antisense sequence that targets the eRNA region above. The antisense sequences are provided as RNA nucleotides. UCUCAUGGGUUUAUGAGAAC [SEQ ID NO: 92].

LNCRNA_569_LNA. 5-10-5 LNA GapmeR contains LNA GapmeR sequences in this structural order: (5) LNA sequences followed by (10) DNA sequences and finally (5) LNA sequences. (lT)#(lC)#(lT)#(lC)#(lA)#(dT)#(dG)#(dG)#(dG)#(dT)#(dT) #(dT)#(dA)#(dT)#(dG)#(lA)#(lG)#(lA)#(lA)#(lC) [SEQ ID NO: 93].

LNCRNA_569_LNA. 5-10-5 MOE GapmeR contains 2'MOE GapmeR sequences in this structural order: (5) 2'MOE sequences followed by (10) DNA sequences and finally (5) 2'MOE sequences. (eT)#(eC)#(eT)#(eC)#(eA)#(dT)#(dG) #(dG)#(dG)#(dT)#(dT)#(dT)#(dA)#(dT)#(dG)#(eA)#(eG)#(eA)#(eA)#(eC) [SEQ ID NO: 94].

LNCRNA_571_LNA. Target 20 nt (5'-3') contains the original eRNA sequence that was selected for GapmeR design (20 nucleotides each). UCUCAUAAACCCAUGAGAUG [SEQ ID NO: 95].

LNCRNA_571_LNA. AS sequence (5'-3') contains the antisense sequence that targets the eRNA region above. The antisense sequences are provided as RNA nucleotides. CAUCUCAUGGGUUUAUGAGA [SEQ ID NO: 96].

LNCRNA_571_LNA. 5-10-5 LNA GapmeR contains LNA GapmeR sequences in this structural order: (5) LNA sequences followed by (10) DNA sequences and finally (5) LNA sequences. (lC)#(lA)#(lT)#(lC)#(lT)#(dC)#(dA)#(dT)#(dG)#(dG)#(dG) #(dT)#(dT)#(dT)#(dA)#(lT)#(lG)#(lA)#(lG)#(lA) [SEQ ID NO: 97].

LNCRNA_571_LNA. 5-10-5 MOE GapmeR contains 2'MOE GapmeR sequences in this structural order: (5) 2'MOE sequences followed by (10) DNA sequences and finally (5) 2'MOE sequences. (eC)#(eA)#(eT)#(eC)#(eT)#(dC)#(dA) #(dT)#(dG)#(dG)#(dG)#(dT)#(dT)#(dT)#(dA)#(eT)#(eG)#(eA)#(eG)#(eA) [SEQ ID NO: 98].

LNCRNA_972_LNA. Target 20 nt (5'-3') contains the original eRNA sequence that was selected for GapmeR design (20 nucleotides each). CCUCACAUCCUACCUGAUCU [SEQ ID NO: 99].

LNCRNA_972_LNA. AS sequence (5'-3') contains the antisense sequence that targets the eRNA region above. The antisense sequences are provided as RNA nucleotides. AGAUCAGGUAGGAUGUGAGG [SEQ ID NO: 100].

LNCRNA_972_LNA. 5-10-5 LNA GapmeR contains LNA GapmeR sequences in this structural order: (5) LNA sequences followed by (10) DNA sequences and finally (5) LNA sequences. (lA)#(lG)#(lA)#(lT)#(lC)#(dA)#(dG)#(dG)#(dT)#(dA)#(dG) #(dG)#(dA)#(dT)#(dG)#(lT)#(lG)#(lA)#(lG)#(lG) [SEQ ID NO: 101].

LNCRNA_972_LNA. 5-10-5 MOE GapmeR contains 2' MOE GapmeR sequences in this structural order: (5) 2'MOE sequences followed by (10) DNA sequences and finally (5) 2'MOE sequences. (eA)#(eG)#(eA)#(eT)#(eC)#(dA)#(dG)#(dG)#(dT)#(dA)#(dG)#(dG)#(dA)#(dT)#(dG)#(eT)#(eG)#(eA)#(eG)#(eG) [SEQ ID NO: 102].

LNCRNA_1027_LNA. Target 20 nt (5'-3') contains the original eRNA sequence that was selected for GapmeR design (20 nucleotides each). UGUGUAGACAGAGUCUCGCU [SEQ ID NO: 103].

LNCRNA_1027_LNA. AS sequence (5'-3') contains the antisense sequence that targets the eRNA region above. The antisense sequences are provided as RNA nucleotides. AGCGAGACUCUGUCUACACA [SEQ ID NO: 104].

LNCRNA_1027_LNA. 5-10-5 LNA GapmeR contains LNA GapmeR sequences in this structural order: (5) LNA sequences followed by (10) DNA sequences and finally (5) LNA sequences. (lA)#(lG)#(lC)#(lG)#(lA)#(dG)#(dA)#(dC)#(dT)#(dC)#(dT) #(dG)#(dT)#(dC)#(dT)#(lA)#(lC)#(lA)#(lC)#(lA) [SEQ ID NO: 105].

LNCRNA_1027_LNA. 5-10-5 MOE GapmeR contains 2'MOE GapmeR sequences in this structural order: (5) 2'MOE sequences followed by (10) DNA sequences and finally (5) 2'MOE sequences. (eA)#(eG)#(eC)#(eG)#(eA)#

(dG)#(dA) #(dC)#(dT)#(dC)#(dT)#(dG)#(dT)#(dC)#(dT)# (eA)#(eC)#(eA)#(eC)#(eA) [SEQ ID NO: 106].

LNCRNA_1207_LNA. Target 20 nt (5'-3') contains the original eRNA sequence that was selected for GapmeR design (20 nucleotides each). UUCACCAUGUUGGU-CAGCUG [SEQ ID NO: 107].

LNCRNA_1207_LNA. AS sequence (5'-3') contains the antisense sequence that targets the eRNA region above. The antisense sequences are provided as RNA nucleotides. CAGCUGACCAACAUGGUGAA [SEQ ID NO: 108].

LNCRNA_1207_LNA. 5-10-5 LNA GapmeR contains LNA GapmeR sequences in this structural order: (5) LNA sequences followed by (10) DNA sequences and finally (5) LNA sequences. (lC)#(lA)#(lG)#(lC)#(lT)#(dG)#(dA)#(dC)# #(dC)#(dA)#(dA) #(dC)#(dA)#(dT)#(dG)#(lG)#(lT)#(lG)# (lA)#(lA) [SEQ ID NO: 109].

LNCRNA_1207_LNA. 5-10-5 MOE GapmeR contains 2'MOE GapmeR sequences in this structural order: (5) 2'MOE sequences followed by (10) DNA sequences and finally (5) 2'MOE sequences. (eC)#(eA)#(eG)#(eC)#(eT)# (dG)#(dA) #(dC)#(dC)#(dA)#(dA)#(dC)#(dA)#(dT)#(dG)# (eG)#(eT)#(eG)#(eA)#(eA) [SEQ ID NO: 110].

LNCRNA_1216_LNA. Target 20 nt (5'-3') contains the original eRNA sequence that was selected for GapmeR design (20 nucleotides each). UUGGUCAGCUGGUC-UUGAAC [SEQ ID NO: 111].

LNCRNA_1216_LNA. AS sequence (5'-3') contains the antisense sequence that targets the eRNA region above. The antisense sequences are provided as RNA nucleotides. GUUCAAGACCAGCUGACCAA [SEQ ID NO: 112].

LNCRNA_1216_LNA. 5-10-5 LNA GapmeR contains LNA GapmeR sequences in this structural order: (5) LNA sequences followed by (10) DNA sequences and finally (5) LNA sequences. (lG)#(lT)#(lT)#(lC)#(lA)#(dA)#(dG)#(dA)# #(dC)#(dC)#(dA) #(dG)#(dC)#(dT)#(dG)#(lA)#(lC)#(lC)# (lA)#(lA) [SEQ ID NO: 113].

LNCRNA_1216_LNA. 5-10-5 MOE GapmeR contains 2'MOE GapmeR sequences in this structural order: (5) 2'MOE sequences followed by (10) DNA sequences and finally (5) 2'MOE sequences. (eG)#(eT)#(eT)#(eC)#(eA)# (dA)#(dG) #(dA)#(dC)#(dC)#(dA)#(dG)#(dC)#(dT)#(dG)# (eA)#(eC)#(eC)#(eA)#(eA) [SEQ ID NO: 114].

LNCRNA_1415_LNA. Target 20 nt (5'-3') contains the original eRNA sequence that was selected for GapmeR design (20 nucleotides each). CUUGGACUGG-CAUAUUUCAA [SEQ ID NO: 115].

LNCRNA_1415_LNA. AS sequence (5'-3') contains the antisense sequence that targets the eRNA region above. The antisense sequences are provided as RNA nucleotides. UUGAAAUAUGCCAGUCCAAG [SEQ ID NO: 116].

LNCRNA_1415_LNA. 5-10-5 LNA GapmeR contains LNA GapmeR sequences in this structural order: (5) LNA sequences followed by (10) DNA sequences and finally (5) LNA sequences. (lT)#(lT)#(lG)#(lA)#(lA)#(dA)#(dT)#(dA)# #(dT)#(dG)#(dC) #(dC)#(dA)#(dG)#(dT)#(lC)#(lC)#(lA)# (lA)#(lG) [SEQ ID NO: 117].

LNCRNA_1415_LNA. 5-10-5 MOE GapmeR contains 2'MOE GapmeR sequences in this structural order: (5) 2'MOE sequences followed by (10) DNA sequences and finally (5) 2'MOE sequences. (eT)#(eT)#(eG)#(eA)#(eA)# (dA)#(dT)#(dA) #(dT)#(dG)#(dC)#(dC)#(dA)#(dG)#(dT)# (eC)#(eC)#(eA)#(eA)#(eG) [SEQ ID NO: 118].

LNCRNA_1421_LNA. Target 20 nt (5'-3') contains the original eRNA sequence that was selected for GapmeR design (20 nucleotides each). CUGGCAUAUUUCAAC-UUCCA [SEQ ID NO: 119].

LNCRNA_1421_LNA. AS sequence (5'-3') contains the antisense sequence that targets the eRNA region above. The antisense sequences are provided as RNA nucleotides. UGGAAGUUGAAAUAUGCCAG [SEQ ID NO: 120].

LNCRNA_1421_LNA. 5-10-5 LNA GapmeR contains LNA GapmeR sequences in this structural order: (5) LNA sequences followed by (10) DNA sequences and finally (5) LNA sequences. (lT)#(lG)#(lG)#(lA)#(lA)#(dG)#(dT)#(dT)# #(dG)#(dA)#(dA) #(dA)#(dT)#(dA)#(dT)#(lG)#(lC)#(lC)# (lA)#(lG) [SEQ ID NO: 121].

LNCRNA_1421_LNA. 5-10-5 MOE GapmeR contains 2'MOE GapmeR sequences in this structural order: (5) 2'MOE sequences followed by (10) DNA sequences and finally (5) 2'MOE sequences. (eT)#(eG)#(eG)#(eA)#(eA)# (dG)#(dT) #(dT)#(dG)#(dA)#(dA)#(dA)#(dT)#(dA)#(dT)# (eG)#(eC)#(eC)#(eA)#(eG) [SEQ ID NO: 122].

LNCRNA_1422_LNA. Target 20 nt (5'-3') contains the original eRNA sequence that was selected for GapmeR design (20 nucleotides each). UGGCAUAUUUCAAC-UUCCAA [SEQ ID NO: 123].

LNCRNA_1422_LNA. AS sequence (5'-3') contains the antisense sequence that targets the eRNA region above. The antisense sequences are provided as RNA nucleotides. UUGGAAGUUGAAAUAUGCCA [SEQ ID NO: 124].

LNCRNA_1422_LNA. 5-10-5 LNA GapmeR contains LNA GapmeR sequences in this structural order: (5) LNA sequences followed by (10) DNA sequences and finally (5) LNA sequences. (lT)#(lT)#(lG)#(lG)#(lA)#(dA)#(dG)#(dT)# #(dT)#(dG)#(dA) #(dA)#(dA)#(dT)#(dA)#(lT)#(lG)#(lC)# (lC)#(lA) [SEQ ID NO: 125].

LNCRNA_1422_LNA. 5-10-5 MOE GapmeR contains 2'MOE GapmeR sequences in this structural order: (5) 2'MOE sequences followed by (10) DNA sequences and finally (5) 2'MOE sequences. (eT)#(eT)#(eG)#(eG)#(eA)# (dA)#(dG) #(dT)#(dT)#(dG)#(dA)#(dA)#(dA)#(dT)#(dA)# (eT)#(eG)#(eC)#(eC)#(eA) [SEQ ID NO: 126].

LNCRNA_1427_LNA. Target 20 nt (5'-3') contains the original eRNA sequence that was selected for GapmeR design (20 nucleotides each). UAUUUCAACUUC-CAAAUUUU [SEQ ID NO: 127].

LNCRNA_1427_LNA. AS sequence (5'-3') contains the antisense sequence that targets the eRNA region above. The antisense sequences are provided as RNA nucleotides. AAAAUUUGGAAGUUGAAAUA [SEQ ID NO: 128].

LNCRNA_1427_LNA. 5-10-5 LNA GapmeR contains LNA GapmeR sequences in this structural order: (5) LNA sequences followed by (10) DNA sequences and finally (5) LNA sequences. (lA)#(lA)#(lA)#(lA)#(lT)#(dT)#(dT)#(dG)# #(dG)#(dA)#(dA) #(dG)#(dT)#(dT)#(dG)#(lA)#(lA)#(lA)# (lT)#(lA) [SEQ ID NO: 129].

LNCRNA_1427_LNA. 5-10-5 MOE GapmeR contains 2' MOE GapmeR sequences in this structural order: (5) 2'MOE sequences followed by (10) DNA sequences and finally (5) 2'MOE sequences. (eA)#(eA)#(eA)#(eA)#(eT)#(dT)#(dT)# (dG) #(dG)#(dA)#(dA)#(dG)#(dT)#(dT)#(dG)#(eA)#(eA)# (eA)#(eT)#(eA) [SEQ ID NO: 130].

LNCRNA_1445_LNA. Target 20 nt (5'-3') contains the original eRNA sequence that was selected for GapmeR design (20 nucleotides each). UUUCCUAUAGGC-UUCAGUUA [SEQ ID NO: 131].

LNCRNA_1445_LNA. AS sequence (5'-3') contains the antisense sequence that targets the eRNA region above. The antisense sequences are provided as RNA nucleotides. UAACUGAAGCCUAUAGGAAA [SEQ ID NO: 132].

LNCRNA_1445_LNA. 5-10-5 LNA GapmeR contains LNA GapmeR sequences in this structural order: (5) LNA sequences followed by (10) DNA sequences and finally (5)

LNA sequences. (lT)#(lA)#(lA)#(lC)#(lT)#(dG)#(dA)#(dA)#(dG)#(dC)#(dC) #(dT)#(dA)#(dT)#(dA)#(lG)#(lG)#(lA)#(lA)#(lA) [SEQ ID NO: 133].

LNCRNA_1445_LNA. 5-10-5 MOE GapmeR contains 2'MOE GapmeR sequences in this structural order: (5) 2'MOE sequences followed by (10) DNA sequences and finally (5) 2'MOE sequences. (eT)#(eA)#(eA)#(eC)#(eT)#(dG)#(dA)#(dA) #(dG)#(dC)#(dC)#(dT)#(dA)#(dT)#(dA)#(eG)#(eG)#(eA)#(eA)#(eA) [SEQ ID NO: 134].

LNCRNA_1447_LNA. Target 20 nt (5'-3') contains the original eRNA sequence that was selected for GapmeR design (20 nucleotides each). UCCUAUAGGCUUCAGUUAAA [SEQ ID NO: 135].

LNCRNA_1447_LNA. AS sequence (5'-3') contains the antisense sequence that targets the eRNA region above. The antisense sequences are provided as RNA nucleotides. UUUAACUGAAGCCUAUAGGA [SEQ ID NO: 136].

LNCRNA_1447_LNA. 5-10-5 LNA GapmeR contains LNA GapmeR sequences in this structural order: (5) LNA sequences followed by (10) DNA sequences and finally (5) LNA sequences. (lT)#(lT)#(lT)#(lA)#(lA)#(dC)#(dT)#(dG)#(dA)#(dA)#(dG) #(dC)#(dC)#(dT)#(dA)#(lT)#(lA)#(lG)#(lG)#(lA) [SEQ ID NO: 137].

LNCRNA_1447_LNA. 5-10-5 MOE GapmeR contains 2'MOE GapmeR sequences in this structural order: (5) 2'MOE sequences followed by (10) DNA sequences and finally (5) 2'MOE sequences. (eT)#(eT)#(eT)#(eA)#(eA)#(dC)#(dT)#(dG) #(dA)#(dA)#(dG)#(dC)#(dC)#(dT)#(dA)#(eT)#(eA)#(eG)#(eG)#(eA) [SEQ ID NO: 138].

LNCRNA_1460_LNA. Target 20 nt (5'-3') contains the original eRNA sequence that was selected for GapmeR design (20 nucleotides each). AGUUAAAAGGAAGGAAUAGA [SEQ ID NO: 139].

LNCRNA_1460_LNA. AS sequence (5'-3') contains the antisense sequence that targets the eRNA region above. The antisense sequences are provided as RNA nucleotides. UCUAUUCCUUCCUUUUAACU [SEQ ID NO: 140].

LNCRNA_1460_LNA. 5-10-5 LNA GapmeR contains LNA GapmeR sequences in this structural order: (5) LNA sequences followed by (10) DNA sequences and finally (5) LNA sequences. (lT)#(lC)#(lT)#(lA)#(lT)#(dT)#(dC)#(dC)#(dT)#(dT)#(dC) #(dC)#(dT)#(dT)#(dT)#(lT)#(lA)#(lA)#(lC)#(lT) [SEQ ID NO: 141].

LNCRNA_1460_LNA. 5-10-5 MOE GapmeR contains 2'MOE GapmeR sequences in this structural order: (5) 2'MOE sequences followed by (10) DNA sequences and finally (5) 2'MOE sequences. (eT)#(eC)#(eT)#(eA)#(eT)#(dT)#(dC)#(dC) #(dT)#(dT)#(dC)#(dC)#(dT)#(dT)#(dT)#(eT)#(eA)#(eA)#(eC)#(eT) [SEQ ID NO: 142].

LNCRNA_1488_LNA. Target 20 nt (5'-3') contains the original eRNA sequence that was selected for GapmeR design (20 nucleotides each). UUCGCCACCAAAGCAAGACU [SEQ ID NO: 143].

LNCRNA_1488_LNA. AS sequence (5'-3') contains the antisense sequence that targets the eRNA region above. The antisense sequences are provided as RNA nucleotides. AGUCUUGCUUUGGUGGCGAA [SEQ ID NO: 144].

LNCRNA_1488_LNA. 5-10-5 LNA GapmeR contains LNA GapmeR sequences in this structural order: (5) LNA sequences followed by (10) DNA sequences and finally (5) LNA sequences. (lA)#(lG)#(lT)#(lC)#(lT)#(dT)#(dG)#(dC)#(dT)#(dT)#(dT) #(dG)#(dG)#(dT)#(dG)#(lG)#(lC)#(lG)#(lA)#(lA) [SEQ ID NO: 145].

LNCRNA_1488_LNA. 5-10-5 MOE GapmeR contains 2'MOE GapmeR sequences in this structural order: (5) 2'MOE sequences followed by (10) DNA sequences and finally (5) 2'MOE sequences. (eA)#(eG)#(eT)#(eC)#(eT)# (dT)#(dG)#(dC) #(dT)#(dT)#(dT)#(dG)#(dG)#(dT)#(dG)#(eG)#(eC)#(eG)#(eA)#(eA) [SEQ ID NO: 146].

LNCRNA_1532_LNA. Target 20 nt (5'-3') contains the original eRNA sequence that was selected for GapmeR design (20 nucleotides each). AGCUGUGGAAACCAGCGUUU [SEQ ID NO: 147].

LNCRNA_1532_LNA. AS sequence (5'-3') contains the antisense sequence that targets the eRNA region above. The antisense sequences are provided as RNA nucleotides. AAACGCUGGUUUCCACAGCU [SEQ ID NO: 148].

LNCRNA_1532_LNA. 5-10-5 LNA GapmeR contains LNA GapmeR sequences in this structural order: (5) LNA sequences followed by (10) DNA sequences and finally (5) LNA sequences. (lA)#(lA)#(lA)#(lC)#(lG)#(dC)#(dT)#(dG) #(dG)#(dT)#(dT) #(dT)#(dC)#(dC)#(dA)#(lC)#(lA)#(lG)#(lC)#(lT) [SEQ ID NO: 149].

LNCRNA_1532_LNA. 5-10-5 MOE GapmeR contains 2'MOE GapmeR sequences in this structural order: (5) 2'MOE sequences followed by (10) DNA sequences and finally (5) 2'MOE sequences. (eA)#(eA)#(eA)#(eC)#(eG)# (dC)#(dT) #(dG)#(dG)#(dT)#(dT)#(dT)#(dC)#(dC)#(dA)#(eC)#(eA)#(eG)#(eC)#(eT) [SEQ ID NO: 150].

LNCRNA_1664_LNA. Target 20 nt (5'-3') contains the original eRNA sequence that was selected for GapmeR design (20 nucleotides each). CUCUGCAAAUAAGGUCGUCU [SEQ ID NO: 151].

LNCRNA_1664_LNA. AS sequence (5'-3') contains the antisense sequence that targets the eRNA region above. The antisense sequences are provided as RNA nucleotides. AGACGACCUUAUUUGCAGAG [SEQ ID NO: 152].

LNCRNA_1664_LNA. 5-10-5 LNA GapmeR contains LNA GapmeR sequences in this structural order: (5) LNA sequences followed by (10) DNA sequences and finally (5) LNA sequences. (lA)#(lG)#(lA)#(lC)#(lG)#(dA)#(dC)#(dC)#(dT)#(dT)#(dA) #(dT)#(dT)#(dT)#(dG)#(lC)#(lA)#(lG)#(lA)#(lG) [SEQ ID NO: 153].

LNCRNA_1664_LNA. 5-10-5 MOE GapmeR contains 2'MOE GapmeR sequences in this structural order: (5) 2'MOE sequences followed by (10) DNA sequences and finally (5) 2'MOE sequences. (eA)#(eG)#(eA)#(eC)#(eG)#(dA)#(dC) #(dC)#(dT)#(dT)#(dA)#(dT)#(dT)#(dT)#(dG)#(eC)#(eA)#(eG)#(eA)#(eG) [SEQ ID NO: 154].

LNCRNA_1683_LNA. Target 20 nt (5'-3') contains the original eRNA sequence that was selected for GapmeR design (20 nucleotides each). UGGGACCCCUGCUUUUCAAG [SEQ ID NO: 155].

LNCRNA_1683_LNA. AS sequence (5'-3') contains the antisense sequence that targets the eRNA region above. The antisense sequences are provided as RNA nucleotides. CUUGAAAAGCAGGGGUCCCA [SEQ ID NO: 156].

LNCRNA_1683_LNA. 5-10-5 LNA GapmeR contains LNA GapmeR sequences in this structural order: (5) LNA sequences followed by (10) DNA sequences and finally (5) LNA sequences. (lC)#(lT)#(lT)#(lG)#(lA)#(dA)#(dA)#(dA) #(dG)#(dC)#(dA) #(dG)#(dG)#(dG)#(dG)#(lT)#(lC)#(lC)#(lC)#(lA) [SEQ ID NO: 157].

LNCRNA_1683_LNA. 5-10-5 MOE GapmeR contains 2'MOE GapmeR sequences in this structural order: (5) 2'MOE sequences followed by (10) DNA sequences and finally (5) 2'MOE sequences. (eC)#(eT)#(eT)#(eG)#(eA)# (dA)#(dA)#(dA) #(dG)#(dC)#(dA)#(dG)#(dG)#(dG)#(dG)#(eT)#(eC)#(eC)#(eC)#(eA) [SEQ ID NO: 158].

LNCRNA_1695_LNA. Target 20 nt (5'-3') contains the original eRNA sequence that was selected for GapmeR design (20 nucleotides each). UUUUCAAGGUUAUUGUCCCA [SEQ ID NO: 159].

LNCRNA_1695_LNA. AS sequence (5'-3') contains the antisense sequence that targets the eRNA region above. The antisense sequences are provided as RNA nucleotides. UGGGACAAUAACCUUGAAAA [SEQ ID NO: 160].

LNCRNA_1695_LNA. 5-10-5 LNA GapmeR contains LNA GapmeR sequences in this structural order: (5) LNA sequences followed by (10) DNA sequences and finally (5) LNA sequences. (lT)#(lG)#(lG)#(lG)#(lA)#(dC)#(dA)# (dA)#(dT)#(dA)#(dA) #(dC)#(dC)#(dT)#(dT)#(lG)#(lA)# (lA)#(lA)#(lA) [SEQ ID NO: 161].

LNCRNA_1695_LNA. 5-10-5 MOE GapmeR contains 2'MOE GapmeR sequences in this structural order: (5) 2'MOE sequences followed by (10) DNA sequences and finally (5) 2'MOE sequences. (eT)#(eG)#(eG)#(eG)#(eA)# (dC)#(dA) #(dA)#(dT)#(dA)#(dA)#(dC)#(dC)#(dT)#(dT)# (eG)#(eA)#(eA)#(eA)#(eA) [SEQ ID NO: 162].

LNCRNA_1706_LNA. Target 20 nt (5'-3') contains the original eRNA sequence that was selected for GapmeR design (20 nucleotides each). AUUGUCCCAGAUGAU-GUAUC [SEQ ID NO: 163].

LNCRNA_1706_LNA. AS sequence (5'-3') contains the antisense sequence that targets the eRNA region above. The antisense sequences are provided as RNA nucleotides. GAUACAUCAUCUGGGACAAU [SEQ ID NO: 164].

LNCRNA_1706_LNA. 5-10-5 LNA GapmeR contains LNA GapmeR sequences in this structural order: (5) LNA sequences followed by (10) DNA sequences and finally (5) LNA sequences. (lG)#(lA)#(lT)#(lA)#(lC)#(dA)#(dT)#(dC) #(dA)#(dT)#(dC) #(dT)#(dG)#(dG)#(dG)#(lA)#(lC)#(lA)# (lA)#(lT) [SEQ ID NO: 165].

LNCRNA_1706_LNA. 5-10-5 MOE GapmeR contains 2'MOE GapmeR sequences in this structural order: (5) 2'MOE sequences followed by (10) DNA sequences and finally (5) 2'MOE sequences. (eG)#(eA)#(eT)#(eA)#(eC)# (dA)#(dT) #(dC)#(dA)#(dT)#(dC)#(dT)#(dG)#(dG)#(dG)# (eA)#(eC)#(eA)#(eA)#(eT) [SEQ ID NO: 166].

LNCRNA_1707_LNA. Target 20 nt (5'-3') contains the original eRNA sequence that was selected for GapmeR design (20 nucleotides each). UUGUCCCAGAUGAU-GUAUCU [SEQ ID NO: 167].

LNCRNA_1707_LNA. AS sequence (5'-3') contains the antisense sequence that targets the eRNA region above. The antisense sequences are provided as RNA nucleotides. AGAUACAUCAUCUGGGACAA [SEQ ID NO: 168].

LNCRNA_1707_LNA. 5-10-5 LNA GapmeR contains LNA GapmeR sequences in this structural order: (5) LNA sequences followed by (10) DNA sequences and finally (5) LNA sequences. (lA)#(lG)#(lA)#(lT)#(lA)#(dC)#(dA)#(dT) #(dC)#(dA)#(dT) #(dC)#(dT)#(dG)#(dG)#(lG)#(lA)#(lC)# (lA)#(lA) [SEQ ID NO: 169].

LNCRNA_1707_LNA. 5-10-5 MOE GapmeR contains 2'MOE GapmeR sequences in this structural order: (5) 2'MOE sequences followed by (10) DNA sequences and finally (5) 2'MOE sequences. (eA)#(eG)#(eA)#(eT)#(eA)# (dC)#(dA)#(dT) #(dC)#(dA)#(dT)#(dC)#(dT)#(dG)#(dG)# (eG)#(eA)#(eC)#(eA)#(eA) [SEQ ID NO: 170].

LNCRNA_1708_LNA. Target 20 nt (5'-3') contains the original eRNA sequence that was selected for GapmeR design (20 nucleotides each). UGUCCCAGAUGAU-GUAUCUU [SEQ ID NO: 171].

LNCRNA_1708_LNA. AS sequence (5'-3') contains the antisense sequence that targets the eRNA region above. The antisense sequences are provided as RNA nucleotides. AAGAUACAUCAUCUGGGACA [SEQ ID NO: 172].

LNCRNA_1708_LNA. 5-10-5 LNA GapmeR contains LNA GapmeR sequences in this structural order: (5) LNA sequences followed by (10) DNA sequences and finally (5) LNA sequences. (lA)#(lA)#(lG)#(lA)#(lT)#(dA)#(dC)# (dA)#(dT)#(dC)#(dA) #(dT)#(dC)#(dT)#(dG)#(lG)#(lG)# (lA)#(lC)#(lA) [SEQ ID NO: 173].

LNCRNA_1708_LNA. 5-10-5 MOE GapmeR contains 2'MOE GapmeR sequences in this structural order: (5) 2'MOE sequences followed by (10) DNA sequences and finally (5) 2'MOE sequences. (eA)#(eA)#(eG)#(eA)#(eT)# (dA)#(dC) #(dA)#(dT)#(dC)#(dA)#(dT)#(dC)#(dT)#(dG)# (eG)#(eG)#(eA)#(eC)#(eA) [SEQ ID NO: 174].

LNCRNA_1709_LNA. Target 20 nt (5'-3') contains the original eRNA sequence that was selected for GapmeR design (20 nucleotides each). GUCCCAGAUGAU-GUAUCUUU [SEQ ID NO: 175].

LNCRNA_1709_LNA. AS sequence (5'-3') contains the antisense sequence that targets the eRNA region above. The antisense sequences are provided as RNA nucleotides. AAAGAUACAUCAUCUGGGAC [SEQ ID NO: 176].

LNCRNA_1709_LNA. 5-10-5 LNA GapmeR contains LNA GapmeR sequences in this structural order: (5) LNA sequences followed by (10) DNA sequences and finally (5) LNA sequences. (lA)#(lA)#(lA)#(lG)#(lA)#(dT)#(dA)# (dC)#(dA)#(dT) #(dC)#(dA)#(dT)#(dC)#(dT)#(lG)#(lG)# (lG)#(lA)#(lC) [SEQ ID NO: 177].

LNCRNA_1709_LNA. 5-10-5 MOE GapmeR contains 2'MOE GapmeR sequences in this structural order: (5) 2'MOE sequences followed by (10) DNA sequences and finally (5) 2'MOE sequences. (eA)#(eA)#(eA)#(eG)#(eA)# (dT)#(dA) #(dC)#(dA)#(dT)#(dC)#(dA)#(dT)#(dC)#(dT)# (eG)#(eG)#(eG)#(eA)#(eC) [SEQ ID NO: 178].

LNCRNA_1710_LNA. Target 20 nt (5'-3') contains the original eRNA sequence that was selected for GapmeR design (20 nucleotides each). UCCCAGAUGAUGUAUC-UUUU [SEQ ID NO: 179].

LNCRNA_1710_LNA. AS sequence (5'-3') contains the antisense sequence that targets the eRNA region above. The antisense sequences are provided as RNA nucleotides. AAAAGAUACAUCAUCUGGGA [SEQ ID NO: 180].

LNCRNA_1710_LNA. 5-10-5 LNA GapmeR contains LNA GapmeR sequences in this structural order: (5) LNA sequences followed by (10) DNA sequences and finally (5) LNA sequences. (lA)#(lA)#(lA)#(lA)#(lG)#(dA)#(dT)# (dA)#(dC)#(dA)#(dT) #(dC)#(dA)#(dT)#(dC)#(lT)#(lG)# (lG)#(lG)#(lA) [SEQ ID NO: 181].

LNCRNA_1710_LNA. 5-10-5 MOE GapmeR contains 2'MOE GapmeR sequences in this structural order: (5) 2'MOE sequences followed by (10) DNA sequences and finally (5) 2'MOE sequences. (eA)#(eA)#(eA)#(eA)#(eG)# (dA)#(dT)#(dA) #(dC)#(dA)#(dT)#(dC)#(dA)#(dT)#(dC)# (eT)#(eG)#(eG)#(eG)#(eA) [SEQ ID NO: 182].

LNCRNA_1775_LNA. Target 20 nt (5'-3') contains the original eRNA sequence that was selected for GapmeR design (20 nucleotides each). AGUGCAGUGGCAAAAUUUCC [SEQ ID NO: 183].

LNCRNA_1775_LNA. AS sequence (5'-3') contains the antisense sequence that targets the eRNA region above. The antisense sequences are provided as RNA nucleotides. GGAAAUUUUGCCACUGCACU [SEQ ID NO: 184].

LNCRNA_1775_LNA. 5-10-5 LNA GapmeR contains LNA GapmeR sequences in this structural order: (5) LNA sequences followed by (10) DNA sequences and finally (5) LNA sequences. (lG)#(lG)#(lA)#(lA)#(lA)#(dT)#(dT)#(dT) #(dT)#(dG)#(dC) #(dC)#(dA)#(dC)#(dT)#(lG)#(lC)#(lA)# (lC)#(lT) [SEQ ID NO: 185].

LNCRNA_1775_LNA. 5-10-5 MOE GapmeR contains 2'MOE GapmeR sequences in this structural order: (5) 2'MOE sequences followed by (10) DNA sequences and finally (5) 2'MOE sequences. (eG)#(eG)#(eA)#(eA)#(eA)#

(dT)#(dT)#(dT) #(dT)#(dG)#(dC)#(dC)#(dA)#(dC)#(dT)#(eG)#(eC)#(eA)#(eC)#(eT) [SEQ ID NO: 186].

LNCRNA_1783_LNA. Target 20 nt (5'-3') contains the original eRNA sequence that was selected for GapmeR design (20 nucleotides each). GGCAAAAUUUCCACCCGCUG [SEQ ID NO: 187].

LNCRNA_1783_LNA. AS sequence (5'-3') contains the antisense sequence that targets the eRNA region above. The antisense sequences are provided as RNA nucleotides. CAGCGGGUGGAAAUUUUGCC [SEQ ID NO: 188].

LNCRNA_1783_LNA. 5-10-5 LNA GapmeR contains LNA GapmeR sequences in this structural order: (5) LNA sequences followed by (10) DNA sequences and finally (5) LNA sequences. (lC)#(lA)#(lG)#(lC)#(lG)#(dG)#(dG)#(dT)#(dG)#(dG) #(dA)#(dA)#(dA)#(dT)#(dT)#(lT)#(lT)#(lG)#(lC)#(lC) [SEQ ID NO: 189].

LNCRNA_1783_LNA. 5-10-5 MOE Gapmer contains 2'MOE GapmeR sequences in this structural order: (5) 2'MOE sequences followed by (10) DNA sequences and finally (5) 2'MOE sequences. (eC)#(eA)#(eG)#(eC)#(eG)#(dG)#(dG) #(dT)#(dG)#(dG)#(dA)#(dA)#(dA)#(dT)#(dT)#(eT)#(eT)#(eG)#(eC)#(eC) [SEQ ID NO: 190].

MALAT1. 5-10-5 LNA GapmeR contains LNA GapmeR sequences in this structural order: (5) LNA sequences followed by (10) DNA sequences and finally (5) LNA sequences. (lG)#(lG)#(lG)#(lT)#(lC)#(dA)#(dG)#(dC)#(dT)#(dG)#(dC)#(dC)#(dA)#(dA) #(dT)#(lG)#(lC)#(lT)#(lA)#(lG) [SEQ ID NO: 191].

MALAT1. 5-10-5 MOE GapmeR contains 2'MOE GapmeR sequences in this structural order: (5) 2'MOE sequences followed by (10) DNA sequences and finally (5) 2'MOE sequences. (eG)#(eG)#(eG)#(eT)#(eC)#(dA)#(dG)#(dC)#(dT)#(dG)#(dC) #(dC)#(dA)#(dA)#(dT)#(eG)#(eC)#(eT)#(eA)#(eG) [SEQ ID NO: 192].

NTC_LNAGapmer. 5-10-5 LNA GapmeR contains LNA GapmeR sequences in this structural order: (5) LNA sequences followed by (10) DNA sequences and finally (5) LNA sequences. (lT)#(lA)#(lA)#(lT)#(lC)#(dG)#(dT)#(dA)#(dT)#(dT)#(dT) #(dG)#(dT)#(dC)#(dA)#(lA)#(lT)#(lC)#(lA)#(lT) [SEQ ID NO: 193].

NTC_LNAGapmer. 5-10-5 MOE GapmeR contains 2'MOE GapmeR sequences in this structural order: (5) 2'MOE sequences followed by (10) DNA sequences and finally (5) 2'MOE sequences. (eT)#(eA)#(eA)#(eT)#(eC)#(dG)#(dT)#(dA) #(dT)#(dT)#(dT)#(dG)#(dT)#(dC)#(dA)#(eA)#(eT)#(eC)#(eA)#(eT) [SEQ ID NO: 194].

List of Embodiments

Specific compositions and methods of targeting enhancer RNAs for the treatment of primary brain tumors have been described. The detailed description in this specification is illustrative and not restrictive or exhaustive. The detailed description is not intended to limit the disclosure to the precise form disclosed. Other equivalents and modifications besides those already described are possible without departing from the inventive concepts described in this specification, as persons having skilled in the molecular neurobiological art will recognize. When the specification or claims recite method steps or functions in an order, alternative embodiments may perform the functions in a different order or substantially concurrently. The inventive subject matter, therefore, is not to be restricted except in the spirit of the disclosure.

When interpreting the disclosure, all terms should be interpreted in the broadest possible manner consistent with the context. Unless otherwise defined, all technical and scientific terms used in this specification have the same meaning as commonly understood by persons having ordinary skill in the molecular neurobiological art. This invention is not limited to the particular methodology, protocols, reagents, and the like described in this specification and, as such, can vary in practice. The terminology used in this specification is not intended to limit the scope of the invention, which is defined solely by the claims.

The terms "comprises" and "comprising" should be interpreted as referring to elements, components, or steps in a non-exclusive manner, indicating that the referenced elements, components, or steps may be present, used, or combined with other elements, components, or steps. The singular terms "a," "an," and "the" include plural referents unless context indicates otherwise. Similarly, the word "or" should cover "and" unless the context indicates otherwise. The abbreviation "e.g." is used to indicate a non-limiting example and is synonymous with the term "for example."

When a range of values is provided, each intervening value, to the tenth of the unit of the lower limit, unless the context dictates otherwise, between the upper and lower limit of that range and any other stated or intervening value in that range of values.

Some embodiments of the technology described can be defined according to the following numbered paragraphs:

1. The GapmeRs disclosed in this patent specification for use in the treatment of brain tumors.
2. The GapmeRs disclosed in this patent specification for use in the treatment of primary brain tumors.
3. A method of targeting enhancer RNAs (eRNA), using synthetic oligonucleotides or a lentivirus carrying a specific shRNA for the treatment of primary brain tumors.
4. The method of embodiment 3, wherein the synthetic oligonucleotides are synthetic RNA oligonucleotides.
5. A synthetic oligonucleotide that hybridizes with enhancer RNAs (eRNAs) that are expressed specifically in glioma stem cells and which expression correlates with decreased survival of patients with glioblastomas.
6. The synthetic oligonucleotide of embodiment 5, wherein the eRNAs are selected from the group consisting of eTMEM88b, eRTP5, and eNINJ1.
7. A method of treating glioma, using synthetic oligonucleotides to knock out the expression of glioma stem cell eRNAs.
8. The method of embodiment 5, wherein the synthetic oligonucleotides are resistant to degradation.
9. The method of embodiment 5, wherein the administration is systemic or intrathecal.
10. A viral vector that delivers an shRNA that targets and inhibits the expression of the eRNA.
11. The viral vector of embodiment 8, wherein the viral vector is a lentivirus.

CITATION LIST

A person having ordinary skill in the molecular neurobiological art can use these patents, patent applications, and scientific references as guidance to predictable results when making and using the invention.

U.S. Pat. No. 10,160,977 B2 (Hnisz et al.), Super-enhancers and methods of use. This patent discloses super-enhancers and related compositions, methods, and agents that are useful for modulating expression of cell type-specific genes that are required for maintenance of cell identity, e.g., embryonic stem cell identity, or maintenance of a disease state (e.g., cancer).

U.S. Pat. Publ. 2015/0337376 A1 (Saint-Andre et al.), Core transcriptional circuitry in human cells and methods of use. This patent publication discloses methods for identifying the core regulatory circuitry or cell identity program of a cell or tissue. This patent publication also discloses related methods of diagnoses, screening, and treatment involving the core regulatory circuitry or cell identity programs identified using the methods.

U.S. Pat. Publ. 2019/0062752 A1 (Young et al.), Transcription factor trapping by RNA in gene regulatory elements. This patent publication discloses methods useful for modulating a target gene's expression by modulating binding between a ribonucleic acid (RNA) transcribed from at least one regulatory element of a target gene and a transcription factor that binds to both the RNA and the regulatory element. This patent publication also discloses methods and assays for identifying agents that interfere with binding between RNA transcribed from at least one regulatory element and a transcription factor that binds to the RNA and to the regulatory element. This patent publication further discloses compositions and methods for modulating gene regulation by modulating condensate formation, composition, maintenance, dissolution, and regulation.

PCT Pat. Publ. WO 2019/183552 A2 (Whitehead Institute for Biomedical Research), Methods and assays for modulating gene transcription by modulating condensates. This patent publication discloses compositions and methods for modulating gene regulation by modulating condensate formation, composition, maintenance, dissolution, and regulation.

Arnold et al., Diversity and emerging roles of enhancer RNA in regulation of gene expression and cell fate. Front. Cell Dev. Biol., 7, 377 (2019). The knockdown of eRNAs has been shown to decrease the accessibility of their respective enhancer regions, suggesting a role for eRNAs in creating or maintaining open chromatin.

Bao et al., Glioma stem cells promote radioresistance by preferential activation of the DNA damage response. Nature, 444(7120), 756-60 (2006). Glioma stem cells are a subset of cells in Glioblastoma Multiforme known to contribute to therapeutic resistance and tumor recurrence. Glioma stem cells present increased phenotypic plasticity (the switch between stem to more differentiated phenotype and de-differentiation back to stem cells) under the influence of the tumor microenvironment and appear to be responsible for resistance to therapeutic interventions.

Ben-Porath et al., An embryonic stem cell-like gene expression signature in poorly differentiated aggressive human tumors. Nature Genetics, 40, 499-507 (2008).

Bhaskar et al., Multifunctional Nanocarriers for diagnostics, drug delivery and targeted treatment across blood-brain barrier: perspectives on tracking and neuroimaging. Part Fibre Toxicol., 7, 3 (2010) Delivery of therapeutic molecules including nucleic acids to the central nervous system and brain tumors is inhibited by the blood-brain barrier, which allows only a small class of drugs or small molecules with high lipid solubility and low molecular mass of <400-500 Daltons to cross the blood-brain barrier.

Bier et al., MicroRNA-137 is downregulated in glioblastoma and inhibits the stemness of glioma stem cells by targeting RTVP-1. Oncotarget, 4(5), 665-76 (2013). In Glioblastoma Multiforme, several miRNAs and lncRNAs have been attributed to disease progression and glioma stem cell growth and renewal.

Blinka et al., Identification of transcribed enhancers by genome-wide chromatin immunoprecipitation sequencing. Methods Mol. Biol., 1468, 91-109 (2017). This publication disclosed methods for the removal of overlap with mRNA production.

Bolzer et al., Three-dimensional maps of all chromosomes in human male fibroblast nuclei and prometaphase rosettes. PLoS Biology, 3(5), e157 (2005). The higher-order eukaryotic genome functional architecture structures and their associated sub-nuclear compartments are recognized by persons having ordinary skill in the molecular neurobiological art as the key components contributing to many aspects of nuclear activities, including DNA transcription Bose et al., RNA Binding to CBP Stimulates Histone Acetylation and Transcription. Cell. 2017; 168(1-2):135-49 e22.

Ceccarelli et al., Molecular profiling reveals biologically discrete subsets and pathways of progression in diffuse glioma. Cell. 2016; 164(3):550-63.

Chen et al., A restricted cell population propagates glioblastoma growth after chemotherapy. Nature, 488(7412), 522-6 (2012). Glioma stem cells are a subset of cells in Glioblastoma Multiforme known to contribute to therapeutic resistance and tumor recurrence. Glioma stem cells present increased phenotypic plasticity (the switch between stem to more differentiated phenotype and de-differentiation back to stem cells) under the influence of the tumor microenvironment and appear to be responsible for resistance to therapeutic interventions.

Cinghu et al., Intragenic enhancers attenuate host gene expression. Mol Cell., 68(1), 104-17 e6 (2017). Most eRNAs are chromatin-associated, rather than free in the nucleoplasm or the cytoplasm.

Cohen et al., IDH1 and IDH2 mutations in gliomas. Curr. Neurol. Neurosci. Rep., 13(5), 345 (2013). Tumor classifications were based on the status of the Isocitrate Dehydrogenase (IDH) gene.

Combs et al., Prognostic significance of IDH-1 and MGMT in patients with glioblastoma: one step forward, and one step back? Radiat. Oncol., 6, 115 (2011). Tumor classifications were based on the status of the Isocitrate Dehydrogenase (IDH) gene Creyghton et al., Histone H3K27ac separates active from poised enhancers and predicts developmental state. Proc. Natl. Acad. Sci. U.S.A., 107(50), 21931-21936 (2010). eRNAs have been associated with promoting certain malignancies through direct and indirect regulation of transcription. eRNAs are implicated in different cells and cellular conditions, including prostate cancer.

De Santa et al., A large fraction of extragenic RNA pol II transcription sites overlap enhancers. PLoS Biol., 8(5), e1000384 (2010). A class of non-coding RNAs produced from the enhancer region, called enhancer RNAs (eRNAs), can regulate gene expression.

Ding et al., Enhancer RNA—P2RY2e induced by estrogen promotes malignant behaviors of bladder cancer. Int. J. Biol. Sci., 14(10), 1268-76 (2018). eRNAs have been associated with promoting certain malignancies through direct and indirect regulation of transcription. eRNAs are implicated in different cells and cellular conditions, including bladder cancer.

Felsberg et al., Prognostic significance of molecular markers and extent of resection in primary glioblastoma patients. Clin. Cancer Res., 15(21), 6683-93 (2009). Tumor classifications were based on the methylation status of 06-methylguanine-DNA methyltransferase (MGMT) promoter.

Feng et al., Methods for the study of long non-coding RNA in cancer cell signaling. Methods Mol. Biol., 1165, 115-43 (2014). This publication describes the subtype classification of Glioblastoma Multiforme.

Francastel et al., Nuclear compartmentalization and gene activity. Nature Review Mol. Cell. Biol. 1(2), 137-43 (2000). Eukaryotic genomes are organized into functional architectures.

Godinho et al., Transvascular delivery of hydrophobically modified siRNAs: Gene silencing in the rat brain upon disruption of the blood-brain barrier. Mol. Ther., 26(11), 2580-91 (2018). Nucleic acid modifications and drug carriers are under development to deliver therapeutic molecules to the central nervous system.

Grondin et al., Chronic, controlled GDNF infusion promotes structural and functional recovery in advanced parkinsonian monkeys. Brain, 125(Pt 10), 2191-201 (2002). Intraventricular delivery of therapeutics via pumps.

Han et al., Interfering with long non-coding RNA MIR22HG processing inhibits glioblastoma progression through suppression of Wnt/beta-catenin signalling. Brain 143(2), 512-30 (2020). In Glioblastoma Multiforme, several miRNAs and lncRNAs have been attributed to disease progression as well as glioma stem cell growth and renewal.

Hu & Smyth, ELDA: extreme limiting dilution analysis for comparing depleted and enriched populations in stem cell and other assays. J. Immunol. Methods, 347(1-2), 70-78 (2009). The in-vitro extreme limiting dilution analysis (ELDA) is a widely used method to determine self-renewal capacity.

Jin et al., Targeting glioma stem cells through combined BMI1 and EZH2 inhibition. Nature Medicine, 23, 1352-1361 (2017).

Johnson et al., Mutational analysis reveals the origin and therapy-driven evolution of recurrent glioma. Science, 343 (6167), 189-93 (2014). Glioma stem cells are a subset of cells in Glioblastoma Multiforme known to contribute to therapeutic resistance and tumor recurrence. Glioma stem cells present increased phenotypic plasticity (the switch between stem to more differentiated phenotype and de-differentiation back to stem cells) under the influence of the tumor microenvironment and appear to be responsible for resistance to therapeutic interventions.

Kaikkonen et al., Remodeling of the enhancer landscape during macrophage activation is coupled to enhancer transcription. Mol Cell. 2013; 51(3):310-25.

The scientific literature has shown that eRNAs from enhancers essential for cellular activation and differentiation activities are typically synthesized before important chromatin remodeling events.

Karavelis et al., Intraventricular administration of morphine for control of intractable cancer pain in 90 patients. Neurosurgery, 39(1), 57-61 (1996), discussion-2. Intraventricular delivery of therapeutics via pumps.

Kim et al., Widespread transcription at neuronal activity-regulated enhancers. Nature, 465(7295), 182-7 (2010). A class of non-coding RNAs produced from the enhancer region, called enhancer RNAs, can regulate gene expression. eRNAs are implicated in different cells and cellular conditions, including neuronal cells.

Kloosterhof et al., Isocitrate dehydrogenase-1 mutations: a fundamentally new understanding of diffuse glioma? Lancet Oncol., 12(1), 83-91 (2011).

Lai et al., Activating RNAs associate with Mediator to enhance chromatin architecture and transcription. Nature. 2013; 494(7438):497-501.

Lam et al., Rev-Erbs repress macrophage gene expression by inhibiting enhancer-directed transcription. Nature, 498 (7455), 511-5 (2013). eRNAs have been associated with promoting certain malignancies through direct and indirect regulation of transcription. eRNAs are implicated in different cells and cellular conditions, including macrophages.

Lathia et al., Cancer stem cells in glioblastoma. Genes Dev., 29(12), 1203-17 (2015). Glioma stem cells are a subset of cells in Glioblastoma Multiforme known to contribute to therapeutic resistance and tumor recurrence. Glioma stem cells present increased phenotypic plasticity (the switch between stem to more differentiated phenotype and de-differentiation back to stem cells) under the influence of the tumor microenvironment and appear to be responsible for resistance to therapeutic interventions.

Lausen & Schumacher. Maximally Selected Rank Statistics for Dose-Response Problems. Biometrical Journal, 44, 131-47 (2002). This publication disclosed methods for the standardized log-rank statistics and maximally selected rank statistics.

Lee et al., Human glioblastoma arises from subventricular zone cells with low-level driver mutations. Nature, 560 (7717), 243-7 (2018). Glioma stem cells present increased phenotypic plasticity (the switch between stem to more differentiated phenotype and de-differentiation back to stem cells) under the influence of the tumor microenvironment and appear to be responsible for resistance to therapeutic interventions.

Lee et al., Tumor stem cells derived from glioblastomas cultured in bFGF and EGF more closely mirror the phenotype and genotype of primary tumors than do serum-cultured cell lines. Cancer Cell, 9, 391-403 (2006).

Li et al., Enhancers as non-coding RNA transcription units: recent insights and future perspectives. Nat Rev Genet. 2016; 17(4):207-23. eRNAs are implicated in different cells and cellular conditions, including neuronal cells.

Li et al., Functional roles of enhancer RNAs for oestrogen-dependent transcriptional activation. Nature, 498 (7455), 516-20 (2013). eRNAs have been associated with promoting certain malignancies through direct and indirect regulation of transcription. eRNAs are implicated in different cells and cellular conditions, including breast cancer.

Liu et al., High expression of enhancer RNA MARC1 or its activation by DHT is associated with the malignant behavior in bladder cancer. Exp. Cell Res., 370(2), 303-11 (2018). eRNAs have been associated with promoting certain malignancies through direct and indirect regulation of transcription. eRNAs are implicated in different cells and cellular conditions, including bladder cancer.

Louis et al., The 2016 World Health Organization classification of tumors of the central nervous system: a summary. Acta Neuropathol. 2016; 131(6):803-20.

Masoudi et al., MiR-21: A key player in glioblastoma pathogenesis. J. Cell. Biochem., 119(2), 1285-90 (2018). Micro RNAs (miRNAs) and long non-coding RNAs (lncRNAs) have been identified in Glioblastoma Multiforme brain tumor (GBM) and speculated to promote the disease.

Mazor et al., The lncRNA TP73-AS1 is linked to aggressiveness in glioblastoma and promotes temozolomide resistance in glioblastoma cancer stem cells. Cell Death Dis., 10(3), 246 (2019). In Glioblastoma Multiforme, several miRNAs and lncRNAs have been attributed to disease progression as well as glioma stem cell growth and renewal.

Misteli, Beyond the sequence: cellular organization of genome function. Cell, 128(4), 787-800 (2007). The higher-order eukaryotic genome functional architecture structures and their associated sub-nuclear compartments are recognized by persons having ordinary skill in the molecular neurobiological art as the key components contributing to many aspects of nuclear activities, including DNA transcription Mizoguchi et al., Clinical implications of microRNAs in human glioblastoma. Front. Oncol. 3, 19 (2013). Micro RNAs (miRNAs) and long non-coding RNAs (lncRNAs) have been identified in Glioblastoma Multiforme brain tumor (GBM) and speculated to promote the disease.

Morton et al., Functional enhancers shape extrachromosomal oncogene amplifications. Cell, 179(6), 1330-41 e13 (2019). Although there is evidence for the presence of eRNAs in Glioblastoma Multiforme and glioma stem cells, their functional implications for the disease have not been published.

Mousavi et al., eRNAs promote transcription by establishing chromatin accessibility at defined genomic loci. Mol Cell., 51(5), 606-17 (2013). The knockdown of eRNAs has been shown to decrease the accessibility of their respective enhancer regions, suggesting a role for eRNAs in creating or maintaining open chromatin.

Parsons et al., An integrated genomic analysis of human glioblastoma multiforme. Science. 2008; 321(5897):1807-12.

Patel et al., Single-cell RNA-seq highlights intratumoral heterogeneity in primary glioblastoma. Science, 344(6190), 1396-401 (2014). Glioma stem cells present increased phenotypic plasticity (the switch between stem to more differentiated phenotype and de-differentiation back to stem cells) under the influence of the tumor microenvironment and appear to be responsible for resistance to therapeutic interventions.

Pesenti et al., The genetic landscape of human glioblastoma and matched primary cancer stem cells reveals intratumour similarity and intertumour heterogeneity. Stem Cells Int., 2617030 (2019). Glioma stem cells present increased phenotypic plasticity (the switch between stem to more differentiated phenotype and de-differentiation back to stem cells) under the influence of the tumor microenvironment and appear to be responsible for resistance to therapeutic interventions.

Rahnamoun et al., RNAs interact with BRD4 to promote enhanced chromatin engagement and transcription activation. Nat Struct Mol Biol. 2018; 25(8):687-97.

Rynkeviciene et al., Non-coding RNAs in glioma. Cancers (Basel). 11(1) (2018). Micro RNAs (miRNAs) and long non-coding RNAs (lncRNAs) have been identified in Glioblastoma Multiforme brain tumor (GBM) and speculated to promote the disease.

Schumacher, BLaM. Maximally selected rank statistics. International Biometric Society, 48(1), 73-85 (1992). This publication disclosed methods for the Shii et al., SERPINB2 is regulated by dynamic interactions with pause-release proteins and enhancer RNAs. Molecular Immunology, 88, 20-31 (2017). Most eRNAs are chromatin-associated, rather than free in the nucleoplasm or the cytoplasm.

Singh et al., Identification of a cancer stem cell in human brain tumors. Cancer Res., 63, 5821-5828 (2003).

Singh, et al., Identification of human brain tumour initiating cells. Nature 432, 396-401 (2004).

SongTao et al., IDH mutations predict longer survival and response to temozolomide in secondary glioblastoma. Cancer Sci. 2012; 103(2):269-73.

Soni et al., CD24 and nanog expression in stem cells in glioblastoma: Correlation with response to chemoradiation and overall survival. Asian Pac. J. Cancer Prev., 18, 2215-2219 (2017).

Southwell et al., Antisense oligonucleotide therapeutics for inherited neurodegenerative diseases, Trends in Molecular Medicine November, Vol. 18, No. 11 (2012).

Souweidane et al., Convection-enhanced delivery for diffuse intrinsic pontine glioma: a single-centre, dose-escalation, phase 1 trial. The Lancet Oncology, 19(8), 1040-50 (2018). Convection enhanced delivery to brain parenchyma for drugs.

Stein et al., Efficient gene silencing by delivery of locked nucleic acid antisense oligonucleotides, unassisted by transfection reagents. Nucleic Acids Res., 38(1), e3 (2010). Inhibition using the GapmeR involved a direct cellular uptake method called gymnosis.

Stupp & Weber, The role of radio- and chemotherapy in glioblastoma. Onkologie, 28, 315-317 (2005).

Stupp et al., Radiotherapy plus concomitant and adjuvant temozolomide for glioblastoma. N. Engl. J. Med., 352(10), 987-96 (2005). Standard therapies include surgery, followed by combinatorial radiotherapy and chemotherapy. Although conventional GBM therapies have been beneficial to some patients, the average tumor recurrence time is seven months.

Thakkar et al., Epidemiologic and molecular prognostic review of glioblastoma. Cancer Epidemiol. Biomarkers Prev., 23(10), 1985-96 (2014). Glioblastoma Multiforme is an aggressive brain tumor with high inter-tumoral and intratumoral heterogeneity and poor prognosis Tsai et al., A muscle-specific enhancer RNA mediates cohesin recruitment and regulates transcription in trans. Mol. Cell, 71(1), 129-41 e8 (2018). eRNAs have been associated with promoting certain malignancies through direct and indirect regulation of transcription. eRNAs are implicated in different cells and cellular conditions, including muscle cells. The knockdown of eRNAs has been shown to decrease the accessibility of their respective enhancer regions, suggesting a role for eRNAs in creating or maintaining open chromatin.

Vecera et al., Long non-coding RNAs in gliomas: From molecular pathology to diagnostic biomarkers and therapeutic targets. Int. J. Mol. Sci., 19(9) (2018). Micro RNAs (miRNAs) and long non-coding RNAs (lncRNAs) have been identified in Glioblastoma Multiforme brain tumor (GBM) and speculated to promote the disease.

Verhaak et al., Integrated genomic analysis identifies clinically relevant subtypes of glioblastoma characterized by abnormalities in PDGFRA, IDH1, EGFR, and NF1. Cancer Cell, 17(1), 98-110 (2010). This publication describes research conducted to classify Glioblastoma Multiforme. This publication describes the subtype classification of Glioblastoma Multiforme by the TCGA-based Verhaak classification scheme.

Wang et al., Tumor evolution of glioma-intrinsic gene expression subtypes associates with immunological changes in the microenvironment. Cancer Cell, 32(1), 42-56 e6 (2017). The research was conducted to classify Glioblastoma Multiforme.

Watanabe et al., IDH1 mutations are early events in the development of astrocytomas and oligodendrogliomas. Am J Pathol. 2009; 174(4):1149-53.

Weller et al., Molecular predictors of progression-free and overall survival in patients with newly diagnosed glioblastoma: a prospective translational study of the German Glioma Network. J. Clin. Oncol., 27(34), 5743-50 (2009). Standard therapies include surgery, followed by combinatorial radiotherapy and chemotherapy. Although conventional GBM therapies have been beneficial to some patients, the average tumor recurrence time is seven months.

Yan et al., IDH1 and IDH2 mutations in gliomas. N. Engl. J. Med., 360(8), 765-73 (2009).

Zepecki et al., Regulation of human glioma cell migration, tumor growth, and stemness gene expression using a Lck targeted inhibitor. Oncogene (2018). The in-vitro extreme limiting dilution analysis (ELDA) is a widely used method to determine self-renewal capacity.

Zhang et al., Transcriptional landscape and clinical utility of enhancer RNAs for eRNA-targeted therapy in cancer. Nature Communications, 10(1), 4562 (2019). Although there is evidence for the presence of eRNAs in Glioblastoma Multiforme and glioma stem cells, their functional implications for the disease have not been published.

Zhao et al., MicroRNA-153 is tumor suppressive in glioblastoma stem cells. Mol. Biol. Rep., 40(4), 2789-98 (2013). In Glioblastoma Multiforme, several miRNAs and lncRNAs have been attributed to disease progression and glioma stem cell growth and renewal.

Zhao et al., Targeted shRNA-loaded liposome complex combined with focused ultrasound for blood brain barrier disruption and suppressing glioma growth. Cancer Lett., 418,147-58 (2018). Nucleic acid modifications and drug carriers are under development to deliver therapeutic molecules to the central nervous system.

Paddison et al., Short hairpin RNAs (shRNAs) induce sequence-specific silencing in mammalian cells. Genes & Development, 16(8), 948-58 (April 2002).

Brummelkamp et al., A system for stable expression of short interfering RNAs in mammalian cells. Science, 296 (5567), 550-3 (April 2002).

Crooke et al., Antisense technology: an overview and prospectus. Nature Reviews Drug Discovery, 1-27 (Mar. 24, 2021).

Current Protocols in Immunology (CPI) (2003). John E. Coligan, ADA M Kruisbeek, David H Margulies, Ethan M Shevach, Warren Strobe, (eds.) John Wiley and Sons, Inc.

Current Protocols in Molecular Biology (CPMB), (2014). Frederick M. Ausubel (ed.), John Wiley and Sons.

Current Protocols in Protein Science (CPPS), (2005). John E. Coligan (ed.), John Wiley and Sons, Inc.

Immunology (2006). Werner Luttmann, published by Elsevier.

Janeway's Immunobiology, (2014). Kenneth Murphy, Allan Mowat, Casey Weaver (eds.), Taylor & Francis Limited.

Laboratory Methods in Enzymology: DNA, (2013). Jon Lorsch (ed.) Elsevier.

Lewin's Genes XI (2014). published by Jones & Bartlett Publishers.

Molecular Biology and Biotechnology: A Comprehensive Desk Reference, (1995). Robert A. Meyers (ed.), published by VCH Publishers, Inc.

Molecular Cloning: A Laboratory Manual, 4th ed., Michael Richard Green and Joseph Sambrook, (2012). Cold Spring Harbor Laboratory Press, Cold Spring Harbor, N.Y., USA.

The Encyclopedia of Molecular Cell Biology and Molecular Medicine, Robert S. Porter et al. (eds.), published by Blackwell Science Ltd., 1999-2012.

The Merck Manual of Diagnosis and Therapy, 19th edition (Merck Sharp & Dohme Corp., 2018).

Pharmaceutical Sciences 231d edition (Elsevier, 2020).

All patents and publications cited throughout this specification are expressly incorporated by reference to disclose and describe the materials and methods that might be used with the technologies described in this specification. The publications discussed are provided solely for their disclosure before the filing date. They should not be construed as an admission that the inventors may not antedate such disclosure under prior invention or for any other reason. If there is an apparent discrepancy between a previous patent or publication and the description provided in this specification, the present specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date supplied by the publisher, the actual publication date shall control.

We claim:

1. A method of targeting enhancer RNAs (eRNA) in a subject in need thereof, the method comprising administering a synthetic modified oligonucleotide for the treatment of primary brain tumors to the subject, wherein the synthetic modified oligonucleotide is a GapmeR comprising SEQ ID NO: 8, SEQ ID NO: 9, SEQ ID NO: 12, SEQ ID NO: 13, SEQ ID NO: 16, SEQ ID NO: 18, SEQ ID NO: 21, or SEQ ID NO: 22.

2. A synthetic modified oligonucleotide that hybridizes with enhancer RNAs (eRNAs) that are expressed specifically in glioma stem cells and which expression correlates with decreased survival of patients with glioblastomas, wherein the synthetic modified oligonucleotide is a GapmeR comprising SEQ ID NO: 8, SEQ ID NO: 9, SEQ ID NO: 12, SEQ ID NO: 13, SEQ ID NO: 16, SEQ ID NO: 18, SEQ ID NO: 21, or SEQ ID NO: 22.

3. The method of claim 1, wherein the synthetic modified oligonucleotide further comprises a synthetic modified oligonucleotide that is a GapmeR selected from the group consisting of the following GapmeRs: SEQ ID NO: 25, SEQ ID NO: 26, SEQ ID NO: 29, SEQ ID NO: 30, SEQ ID NO: 33, SEQ ID NO: 34, SEQ ID NO: , SEQ ID NO: 37, SEQ ID NO: 38, SEQ ID NO: 41, SEQ ID NO: 42, SEQ ID NO: 45, SEQ ID NO: 46, SEQ ID NO: 49, SEQ ID NO: 50, SEQ ID NO: 53, SEQ ID NO: 54, SEQ ID NO: 57, SEQ ID NO: 58, SEQ ID NO: 61, SEQ ID NO: 62, SEQ ID NO: 65, SEQ ID NO: 66, SEQ ID NO: 69, SEQ ID NO: 70, SEQ ID NO: 73, SEQ ID NO: 74, SEQ ID NO: 77, SEQ ID NO: 78, SEQ ID NO: 81, SEQ ID NO: 82, SEQ ID NO: 85, SEQ ID NO: 86, SEQ ID NO: 89, SEQ ID NO: 90, SEQ ID NO: 93, SEQ ID NO: 94, SEQ ID NO: 97, SEQ ID NO: 98, SEQ ID NO: 101, SEQ ID NO: 102, SEQ ID NO: 105, SEQ ID NO: 106, SEQ ID NO: 109, SEQ ID NO: 110, SEQ ID NO: 113, SEQ ID NO: 114, SEQ ID NO: 117, SEQ ID NO: 118, SEQ ID NO: 121, SEQ ID NO: 122, SEQ ID NO: 125, SEQ ID NO: 126, SEQ ID NO: 129, SEQ ID NO: 130, SEQ ID NO: 133, SEQ ID NO: 134, SEQ ID NO: 137, SEQ ID NO: 138, SEQ ID NO: 141, SEQ ID NO: 142, SEQ ID NO: 145, SEQ ID NO: 146, SEQ ID NO: 149, SEQ ID NO: 150, SEQ ID NO: 153, SEQ ID NO: 154, SEQ ID NO: 157, SEQ ID NO: 158, SEQ ID NO: 161, SEQ ID NO: 162, SEQ ID NO: 165, SEQ ID NO: 166, SEQ ID NO: 169, SEQ ID NO: 170, SEQ ID NO: 173, SEQ ID NO: 174, SEQ ID NO: 177, SEQ ID NO: 178, SEQ ID NO: 181, SEQ ID NO: 182, SEQ ID NO: 185, SEQ ID NO: 186, SEQ ID NO: 189, SEQ ID NO: 190, SEQ ID NO: 191, SEQ ID NO: 192, SEQ ID NO: 193, and SEQ ID NO: 194.

4. The synthetic modified oligonucleotide of claim 2, further comprising a synthetic modified oligonucleotide that is a GapmeRs selected from the group consisting of the following GapmeRs: SEQ ID NO: 25, SEQ ID NO: 26, SEQ ID NO: 29, SEQ ID NO: 30, SEQ ID NO: 33, SEQ ID NO: 34, SEQ ID NO: , SEQ ID NO: 37, SEQ ID NO: 38, SEQ ID NO: 41, SEQ ID NO: 42, SEQ ID NO: 45, SEQ ID NO: 46, SEQ ID NO: 49, SEQ ID NO: 50, SEQ ID NO: 53, SEQ ID NO: 54, SEQ ID NO: 57, SEQ ID NO: 58, SEQ ID NO: 61, SEQ ID NO: 62, SEQ ID NO: 65, SEQ ID NO: 66, SEQ ID NO: 69, SEQ ID NO: 70, SEQ ID NO: 73, SEQ ID NO: 74, SEQ ID NO: 77, SEQ ID NO: 78, SEQ ID NO: 81, SEQ ID NO: 82, SEQ ID NO: 85, SEQ ID NO: 86, SEQ ID NO: 89, SEQ ID NO: 90, SEQ ID NO: 93, SEQ ID NO: 94, SEQ ID NO: 97, SEQ ID NO: 98, SEQ ID NO: 101, SEQ ID NO: 102, SEQ ID NO: 105, SEQ ID NO: 106, SEQ ID NO: 109, SEQ ID NO: 110, SEQ ID NO: 113, SEQ ID NO: 114, SEQ ID NO: 117, SEQ ID NO: 118, SEQ ID NO: 121, SEQ ID NO: 122, SEQ ID NO: 125, SEQ ID NO: 126, SEQ ID NO: 129, SEQ ID NO: 130, SEQ ID NO: 133, SEQ ID NO: 134, SEQ ID NO: 137, SEQ ID NO: 138, SEQ ID NO: 141, SEQ ID NO: 142, SEQ ID NO: 145, SEQ ID NO: 146, SEQ ID NO: 149, SEQ ID NO: 150, SEQ ID NO: 153, SEQ ID NO: 154, SEQ ID NO: 157, SEQ ID NO: 158, SEQ ID NO: 161, SEQ ID NO: 162, SEQ ID NO: 165, SEQ ID NO: 166, SEQ ID NO: 169, SEQ ID NO: 170, SEQ ID NO: 173, SEQ ID NO: 174, SEQ ID NO: 177, SEQ ID NO: 178, SEQ ID NO: 181, SEQ ID NO: 182, SEQ ID NO: 185, SEQ ID NO: 186, SEQ ID NO: 189, SEQ ID NO: 190, SEQ ID NO: 191, SEQ ID NO: 192, SEQ ID NO: 193, and SEQ ID NO: 194.

\* \* \* \* \*

SEQUENCE LISTING

<160> NUMBER OF SEQ ID NOS: 194

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgggagtaga agttgg                                                      16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcgtctaggc tggcag                                                      16

<210> SEQ ID NO 3
<211> LENGTH: 668
<212> TYPE: DNA
<213> ORGANISM: Homo sapiens

<400> SEQUENCE: 3
atctagtaca tcatattgcc agcagggctc agcctgtgac cagcaaggtc tgggctccgt        60
ctggggccag ggtcaaggct cattccgtgg ccttgagcac agcctggtgt gtggctgggt       120
cgagtccagc agaagtctcg gggttttcca gcctccatcc gagtccggct ttgatgcctt       180
tcctggtcag acaggagccg ggccagtggc caagctgcca ggatggcttc ccgggggccg       240
cggccgcctt ccttcccctc ctgcccgggc tggctctggt cgccactagg ggttgaagat       300
gagggctctc ctgggaagct cttggctgag gatccgcctg gtcccggagc cgtgaaaaca       360
acagctgggc ctggtggggg tggggaggct gagcggagag ccagctccc ttggctgctg        420 ggcagggtct tctgtccaca gctgcctcag gcggctgttt ccaaaggtgt ttccagcttc       480
ccaggcccac cctgaggccc cgcaccgcca gggaggtgga aggcacggag cagcgaagcc       540
cggccccggc ccggccgcc cgaccagctc acagaggaac acctgtgggg gggcctgtgg        600
gcggttcaca gagggatgta ggaacgtgcc tgtgggaggc cgtagccccg agagcagag        660 gcctggcc                                                              668

<210> SEQ ID NO 4
<211> LENGTH: 291
<212> TYPE: DNA
<213> ORGANISM: Homo sapiens

<400> SEQUENCE: 4
cggcagcaac actgccacgc gaatccgcgc cggccaatca gcatggccag gggcggggct        60
tccctgaggc gcgccgagag gcggtggccc acttccggca ataatcgcct ggtcgccgtc       120
aggtgccggc ccaggtggca ggcgcgcccg ttgggcactg ggggacgcgg gcgcgtcagg       180
tgaagactgg gggctgcagg cgcgctaggt aggtacgggg tgccgcgggc gcgtcaggtg       240
aagactgggc gccgcaggcg ccttaggtga agattgggga tcgcgggcgc g                291

<210> SEQ ID NO 5
<211> LENGTH: 1832
<212> TYPE: DNA
<213> ORGANISM: Homo sapiens

<400> SEQUENCE: 5
agaattgcct gaaccagggg ttggaggttg cagcgggtgg aaattttgcc actgcactcc        60
agcctgggtg acagagtgag accctgtctc aaagaaaaaa aaaaaaagat acatcatctg       120
ggacaataac cttgaaaagc agggggtccca gacgaccttta tttgcagaga atgcgactgc       180
agacggcaag caggggggca tgcccttcgc tctctgtcct ctgctctttg ccccggccac       240
tgtcggcctc atctgaaggc cacctgtgcc tcacggtctg aaaacgctgg tttccacagc       300
tgcttctcct tccaaatttc cctggagtct tgctttggtg gcgaacctct ggttctattc       360 cttccttta actgaagcct ataggaaaaa tttggaagtt gaaatatgcc agtccaagga       420
aggtggacgt ggagttctga gggtgggggt gctgccaggg aagtggcact gtgcagggga       480
ccgcccctgg gaccccctgg ttcctgtcaa gagcaggtag gggctgggcg cggtggctca       540

```
cgcctataat cccagcactt tgggaggtca aggagagtgg atcacctaag gtcaggagtt    600
caagaccagc tgaccaacat ggtgaaaccc cgtctctact aaaaatacaa aaattagctg    660
ggcgtggtgg caggcgccta taatcccagg tattcaggag gctgaggcag gagaatagct    720
tgaacccagg aggcagaggt tgcagtgagc tgagatcgca ccactgcact ccagcctggg    780
cgacagagcg agactctgtc tacacacaca cacacacaca cacagacaca cacacacaca    840
cagatcaggt aggatgtgag gtgtgtcctc atggccggac atggggtggg tggggccaaa    900
caaccacagg gactcgtcct gtggccactg ctgctcagga agtggatccc aaggagcaga    960
gtcgccagac ccctcagttc ccagctccac atttaaggca ggtctggcca tgagccaggc   1020
ctctgcatgt gacctggggc ctcactgtgg catggctgcc tgtcccacct gtggatgttg   1080
cctgtgctgt gtagaagcca catagcctcc ggggcggctc cccagaatgc cacatttcct   1140
gtctctggct ctgatggcgt ctaggctggc agggtcccg gccccagcag tactgttgcc    1200
gggcagagct cagggccacg tgcagttggg tctggctgag agcatctcat gggtttatga   1260
gaacccttcc agcacaaagg ggcatttatc aggcagggat ggcatgtctt ggtctgaaca   1320
caggaaacac agaaatagcc tttcacagag tgccagcagg gctgggctcg cctgctgtgg   1380
agggtgtcgg ctttccaact ccttctccaa gctgtgcgac ccgtccatgt tccctgtga    1440 gttgttctgt cccagacagg gcattccctg agaacgctcc tgctgcaact ggagggagag   1500
aggcagggag gggaaagggg aagacttgca gggagaagga agaagggaga cagatggaga   1560
cagacagaag gagggatgga agaaatgaga gagagagagg gagggagatg gaaacataga   1620
ttgtctccac tgtgacaccc tgcctccatg gttctccatg atgggaatgg aattcatgtc   1680
tcacctggca gcaagggtct ccacaatatg acttcacctt ctttctctta gtaaggcgag   1740
agcagacagg cagacactcc aggaagtaac tgatgtgtcc ctgaaaatgc ctgtctttcc   1800
cagcttgtac aactttgctt gtgttatttc tt                                 1832
```

<210> SEQ ID NO 6
<211> LENGTH: 20
<212> TYPE: RNA
<213> ORGANISM: Unknown
<220> FEATURE:
<223> OTHER INFORMATION: Description of Unknown:
    target sequence

<400> SEQUENCE: 6
uguacaagcu gggaaagaca                                                 20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 7
ugucuuuccc agcuuguaca                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 8
tgtctttccc agcttgtaca                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 9
tgtctttccc agcttgtaca                                                  20

<210> SEQ ID NO 10
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 10
cugggaaaga caggcauuuu                                                  20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaaugccug ucuuucccag                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 12
aaaatgcctg tctttcccag                                                      20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 13
aaaatgcctg tctttcccag                                                      20

<210> SEQ ID NO 14
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 14
caggcauuuu cagggacaca                                                      20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ugugucccug aaaaugccug                                                      20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
```

<223> OTHER INFORMATION: Locked nucleic acid

<400> SEQUENCE: 16
tgtgtccctg aaaatgcctg                                        20

<210> SEQ ID NO 17

<400> SEQUENCE: 17

000

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 18
tgtgtccctg aaaatgcctg                                        20

<210> SEQ ID NO 19
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 19
ucagggacac aucaguuacu                                        20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aguaacugau gugcccuga                                         20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:

```
<221> NAME/KEY: modified_base
<222> LOCATION: (16)..(20)
<223> OTHER INFORMATION: Locked nucleic acid

<400> SEQUENCE: 21
agtaactgat gtgtccctga                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 22
agtaactgat gtgtccctga                                                    20

<210> SEQ ID NO 23
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 23
agggacacau caguuacuuc                                                    20

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gaaguaacug augugcccu                                                     20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 25
```

-continued

```
gaagtaactg atgtgtccct                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 26
gaagtaactg atgtgtccct                                                  20

<210> SEQ ID NO 27
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 27
aaagaaggug aagucauauu                                                  20

<210> SEQ ID NO 28
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aauaugacuu caccuucuuu                                                  20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 29
aatatgactt caccttcttt                                                  20

<210> SEQ ID NO 30
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 30
aatatgactt caccttcttt                                                 20

<210> SEQ ID NO 31
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 31
gaagucauau uguggagacc                                                 20

<210> SEQ ID NO 32
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ggucuccaca auaugacuuc                                                 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 33
ggtctccaca atatgacttc                                                 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 34
ggtctccaca atatgacttc                                               20

<210> SEQ ID NO 35
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 35
gcugccaggu gagacaugaa                                               20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uucaugucuc accuggcagc                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 37
ttcatgtctc acctggcagc                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 38
ttcatgtctc acctggcagc                                                 20

<210> SEQ ID NO 39
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 39
ugagacauga auuccauucc                                                 20

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggaauggaau ucaugucuca                                                 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 41
ggaatggaat tcatgtctca                                                 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
```

```
<222> LOCATION: (16)..(20)
<223> OTHER INFORMATION: 2'MOE nucleotide

<400> SEQUENCE: 42
ggaatggaat tcatgtctca                                           20

<210> SEQ ID NO 43
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 43
ugucacagug gagacaaucu                                           20

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
agauugucuc cacugugaca                                           20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 45
agattgtctc cactgtgaca                                           20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 46
```
agattgtctc cactgtgaca					20

<210> SEQ ID NO 47
<211> LENGTH: 20
<212> TYPE: RNA
<213> ORGANISM: Unknown
<220> FEATURE:
<223> OTHER INFORMATION: Description of Unknown:
     target sequence

<400> SEQUENCE: 47
ucuuccaucc cuccuucugu					20

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 48
acagaaggag ggauggaaga					20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 49
acagaaggag ggatggaaga					20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 50
acagaaggag ggatggaaga					20

<210> SEQ ID NO 51
<211> LENGTH: 20

```
<212> TYPE: RNA
<213> ORGANISM: Unknown
<220> FEATURE:
<223> OTHER INFORMATION: Description of Unknown:
      target sequence

<400> SEQUENCE: 51
ucugggacag aacaacucac                                              20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gugaguuguu cugucccaga                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 53
gtgagttgtt ctgtcccaga                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 54
gtgagttgtt ctgtcccaga                                              20

<210> SEQ ID NO 55
<211> LENGTH: 20
<212> TYPE: RNA
<213> ORGANISM: Unknown
<220> FEATURE:
<223> OTHER INFORMATION: Description of Unknown:
      target sequence
```

<400> SEQUENCE: 55
cugugaaagg cuauuucugu                                               20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
acagaaauag ccuuucacag                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 57
acagaaatag cctttcacag                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 58
acagaaatag cctttcacag                                               20

<210> SEQ ID NO 59
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 59
aaggcuauuu cuguguuucc                                               20

```
<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ggaaacacag aaauagccuu                                                    20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 61
ggaaacacag aaatagcctt                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 62
ggaaacacag aaatagcctt                                                    20

<210> SEQ ID NO 63
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 63
uucuguguuu ccuguguuca                                                    20

<210> SEQ ID NO 64
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 64
ugaacacagg aaacacagaa                                                   20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 65
tgaacacagg aaacacagaa                                                   20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 66
tgaacacagg aaacacagaa                                                   20

<210> SEQ ID NO 67
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 67
ucuguguuuc cuguguucag                                                   20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
```
cugaacacag gaaacacaga                                            20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 69
ctgaacacag gaaacacaga                                            20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 70
ctgaacacag gaaacacaga                                            20

<210> SEQ ID NO 71
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 71
cagaccaaga caugccaucc                                            20

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ggauggcaug ucuuggucug                                            20

<210> SEQ ID NO 73

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 73
ggatggcatg tcttggtctg                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 74
ggatggcatg tcttggtctg                                              20

<210> SEQ ID NO 75
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 75
caugccaucc cugccugaua                                              20

<210> SEQ ID NO 76
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uaucaggcag ggauggcaug                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 77
tatcaggcag ggatggcatg                                                    20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 78
tatcaggcag ggatggcatg                                                    20

<210> SEQ ID NO 79
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 79
ccugccugau aaaugcccccu                                                   20

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
aggggcauuu aucaggcagg                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 81
aggggcattt atcaggcagg                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 82
aggggcattt atcaggcagg                                               20

<210> SEQ ID NO 83
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 83
uuugugcugg aaggguucuc                                               20

<210> SEQ ID NO 84
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
gagaacccuu ccagcacaaa                                               20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
```

```
<222> LOCATION: (16)..(20)
<223> OTHER INFORMATION: Locked nucleic acid

<400> SEQUENCE: 85
gagaaccctt ccagcacaaa                                               20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 86
gagaaccctt ccagcacaaa                                               20

<210> SEQ ID NO 87
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 87
uugugcugga aggguucuca                                               20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ugagaacccu uccagcacaa                                               20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 89
```
tgagaaccct tccagcacaa                                           20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 90
tgagaaccct tccagcacaa                                           20

<210> SEQ ID NO 91
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 91
guucucauaa acccaugaga                                           20

<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ucucaugggu uuaugagaac                                           20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 93
tctcatgggt ttatgagaac                                           20

<210> SEQ ID NO 94
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 94
tctcatgggt ttatgagaac                                                 20

<210> SEQ ID NO 95
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 95
ucucauaaac ccaugagaug                                                 20

<210> SEQ ID NO 96
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
caucucaugg guuuaugaga                                                 20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 97
catctcatgg gtttatgaga                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 98
catctcatgg gtttatgaga                                                   20

<210> SEQ ID NO 99
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 99
ccucacaucc uaccugaucu                                                   20

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
agaucaggua ggaugugagg                                                   20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 101
agatcaggta ggatgtgagg                                                   20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 102
agatcaggta ggatgtgagg                                               20

<210> SEQ ID NO 103
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 103
uguguagaca gagucucgcu                                               20

<210> SEQ ID NO 104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
agcgagacuc ugucuacaca                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 105
agcgagactc tgtctacaca                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
```

<223> OTHER INFORMATION: 2'MOE nucleotide

<400> SEQUENCE: 106
agcgagactc tgtctacaca                                          20

<210> SEQ ID NO 107
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 107
uucaccaugu uggucagcug                                          20

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
cagcugacca acauggugaa                                          20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 109
cagctgacca acatggtgaa                                          20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 110
cagctgacca acatggtgaa                                          20

<210> SEQ ID NO 111
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 111
uuggucagcu ggucuugaac                                                20

<210> SEQ ID NO 112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
guucaagacc agcugaccaa                                                20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 113
gttcaagacc agctgaccaa                                                20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 114
gttcaagacc agctgaccaa                                                20

<210> SEQ ID NO 115
<211> LENGTH: 20
<212> TYPE: RNA

```
<213> ORGANISM: Unknown
<220> FEATURE:
<223> OTHER INFORMATION: Description of Unknown:
      target sequence

<400> SEQUENCE: 115
cuuggacugg cauauuucaa                                              20

<210> SEQ ID NO 116
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uugaaauaug ccaguccaag                                              20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 117
ttgaaatatg ccagtccaag                                              20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 118
ttgaaatatg ccagtccaag                                              20

<210> SEQ ID NO 119
<211> LENGTH: 20
<212> TYPE: RNA
<213> ORGANISM: Unknown
<220> FEATURE:
<223> OTHER INFORMATION: Description of Unknown:
      target sequence
```

```
<400> SEQUENCE: 119
cuggcauauu ucaacuucca                                                  20

<210> SEQ ID NO 120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uggaaguuga aauaugccag                                                  20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 121
tggaagttga aatatgccag                                                  20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 122
tggaagttga aatatgccag                                                  20

<210> SEQ ID NO 123
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 123
uggcauauuu caacuuccaa                                                  20
```

```
<210> SEQ ID NO 124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uuggaaguug aaauaugcca                                                    20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 125
ttggaagttg aaatatgcca                                                    20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 126
ttggaagttg aaatatgcca                                                    20

<210> SEQ ID NO 127
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 127
uauuucaacu uccaaauuuu                                                    20

<210> SEQ ID NO 128
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 128
aaaauuugga aguugaaaua                                                     20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 129
aaaatttgga agttgaaata                                                     20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 130
aaaatttgga agttgaaata                                                     20

<210> SEQ ID NO 131
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 131
uuuccuauag gcuucaguua                                                     20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
```
uaacugaagc cuauaggaaa                                              20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 133
taactgaagc ctataggaaa                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 134
taactgaagc ctataggaaa                                              20

<210> SEQ ID NO 135
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 135
uccuauaggc uucaguuaaa                                              20

<210> SEQ ID NO 136
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uuuaacugaa gccuauagga                                              20

<210> SEQ ID NO 137
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 137
tttaactgaa gcctatagga                                                    20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 138
tttaactgaa gcctatagga                                                    20

<210> SEQ ID NO 139
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 139
aguuaaaagg aaggaauaga                                                    20

<210> SEQ ID NO 140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ucuauuccuu ccuuuuaacu                                                    20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 141
tctattcctt cctttaact                                                    20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 142
tctattcctt cctttaact                                                    20

<210> SEQ ID NO 143
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 143
uucgccacca aagcaagacu                                                   20

<210> SEQ ID NO 144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
agucuugcuu ugguggcgaa                                                   20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 145
agtcttgctt tggtggcgaa                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 146
agtcttgctt tggtggcgaa                                              20

<210> SEQ ID NO 147
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 147
agcuguggaa accagcguuu                                              20

<210> SEQ ID NO 148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
aaacgcuggu uuccacagcu                                              20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
```

```
<223> OTHER INFORMATION: Locked nucleic acid

<400> SEQUENCE: 149
aaacgctggt tccacagct                                            20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 150
aaacgctggt tccacagct                                            20

<210> SEQ ID NO 151
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 151
cucugcaaau aaggucgucu                                           20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
agacgaccuu auuugcagag                                           20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 153 agacgaccett atttgcagag                                          20
```

```
<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 154
agacgacctt atttgcagag                                              20

<210> SEQ ID NO 155
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 155
ugggaccccu gcuuuucaag                                              20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cuugaaaagc agggguccca                                              20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 157
cttgaaaagc aggggtccca                                              20

<210> SEQ ID NO 158
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 158
cttgaaaagc aggggtccca                                              20

<210> SEQ ID NO 159
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 159
uuuucaaggu uauuguccca                                              20

<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ugggacaaua accuugaaaa                                              20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 161
tgggacaata accttgaaaa                                              20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 162
tgggacaata accttgaaaa                                                   20

<210> SEQ ID NO 163
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 163
auugucccag augauguauc                                                   20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
gauacaucau cugggacaau                                                   20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 165
gatacatcat ctgggacaat                                                   20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
```

```
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 166
gatacatcat ctgggacaat                                                  20

<210> SEQ ID NO 167
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 167
uugucccaga ugauguaucu                                                  20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
agauacauca ucugggacaa                                                  20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 169
agatacatca tctgggacaa                                                  20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide
```

<400> SEQUENCE: 170
agatacatca tctgggacaa                                              20

<210> SEQ ID NO 171
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 171
ugucccagau gauguaucuu                                              20

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
aagauacauc aucugggaca                                              20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 173
aagatacatc atctgggaca                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 174
aagatacatc atctgggaca                                              20

```
<210> SEQ ID NO 175
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 175
gucccagaug auguaucuuu                                                 20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
aaagauacau caucugggac                                                 20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 177
aaagatacat catctgggac                                                 20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 178
aaagatacat catctgggac                                                 20

<210> SEQ ID NO 179
<211> LENGTH: 20
<212> TYPE: RNA
<213> ORGANISM: Unknown
```

```
<220> FEATURE:
<223> OTHER INFORMATION: Description of Unknown:
      target sequence

<400> SEQUENCE: 179
ucccagauga uguaucuuuu                                                  20

<210> SEQ ID NO 180
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
aaaagauaca ucaucuggga                                                  20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 181
aaaagataca tcatctggga                                                  20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 182
aaaagataca tcatctggga                                                  20

<210> SEQ ID NO 183
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 183
```

```
agugcagugg caaaauuucc                                              20

<210> SEQ ID NO 184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
ggaaauuuug ccacugcacu                                              20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 185
ggaaattttg ccactgcact                                              20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 186
ggaaattttg ccactgcact                                              20

<210> SEQ ID NO 187
<211> LENGTH: 20
<212> TYPE: RNA
<213> ORGANISM: Unknown
<220> FEATURE:
<223> OTHER INFORMATION: Description of Unknown:
      target sequence

<400> SEQUENCE: 187
ggcaaaauuu ccacccgcug                                              20

<210> SEQ ID NO 188
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
cagcgggugg aaauuuugcc                                                  20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 189
cagcgggtgg aaattttgcc                                                  20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 190
cagcgggtgg aaattttgcc                                                  20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid
```

<400> SEQUENCE: 191
gggtcagctg ccaatgctag                                                 20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 192
gggtcagctg ccaatgctag                                                 20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: Locked nucleic acid
<220> FEATURE:
<221> NAME/KEY: modified_base
<222> LOCATION: (16)..(20)
<223> OTHER INFORMATION: Locked nucleic acid

<400> SEQUENCE: 193
taatcgtatt tgtcaatcat                                                 20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'MOE nucleotide
<220> FEATURE:
<221> NAME/KEY: modified_base
<222> LOCATION: (16)..(20)
<223> OTHER INFORMATION: 2'MOE nucleotide

<400> SEQUENCE: 194
taatcgtatt tgtcaatcat                                                 20